United States Patent

Hosoi

[11] Patent Number: 6,045,225
[45] Date of Patent: Apr. 4, 2000

[54] OPTOMETRIC APPARATUS

[75] Inventor: Yoshinobu Hosoi, Aichi, Japan

[73] Assignee: Nidek Co., Ltd., Aichi, Japan

[21] Appl. No.: 09/021,270

[22] Filed: Feb. 10, 1998

[30] Foreign Application Priority Data

| Feb. 10, 1997 | [JP] | Japan | 9-041479 |
| Feb. 10, 1997 | [JP] | Japan | 9-041480 |
| Feb. 10, 1997 | [JP] | Japan | 9-041481 |

[51] Int. Cl.$^7$ .................................................. A61B 3/00
[52] U.S. Cl. ............................................................ 351/200
[58] Field of Search .................................. 351/200, 215, 351/220, 222, 232, 237, 239, 240, 241, 244, 204, 205, 161; 425/384

[56] References Cited

U.S. PATENT DOCUMENTS

| 5,444,504 | 8/1995 | Kobayashi et al. | 351/237 |
| 5,610,671 | 3/1997 | Hosoi et al. | 351/200 |
| 5,627,612 | 5/1997 | Hayashi | 351/200 |
| 5,662,951 | 9/1997 | Greshes | 425/384 |
| 5,715,031 | 2/1998 | Roffman et al. | 351/161 |

*Primary Examiner*—George Manuel
*Attorney, Agent, or Firm*—Sughrue, Mion, Zinn, Macpeak & Seas, PLLC

[57] ABSTRACT

An optometric apparatus capable of effecting the examination efficiently by reducing the amount of power adjustment by the examiner. A multiplicity of actual prescription powers, and perfect correction powers and adjustment factor data on the basis of which an examiner determined the actual prescription power in the past are stored. In estimating a prescription power by making adjustments to a correction power in relation to a perfect correction power on the basis of adjustment factor data, a correction amount used in making the adjustments to correction power is made varied by statistically processing the multiplicity of stored data.

14 Claims, 21 Drawing Sheets

FIG. 9
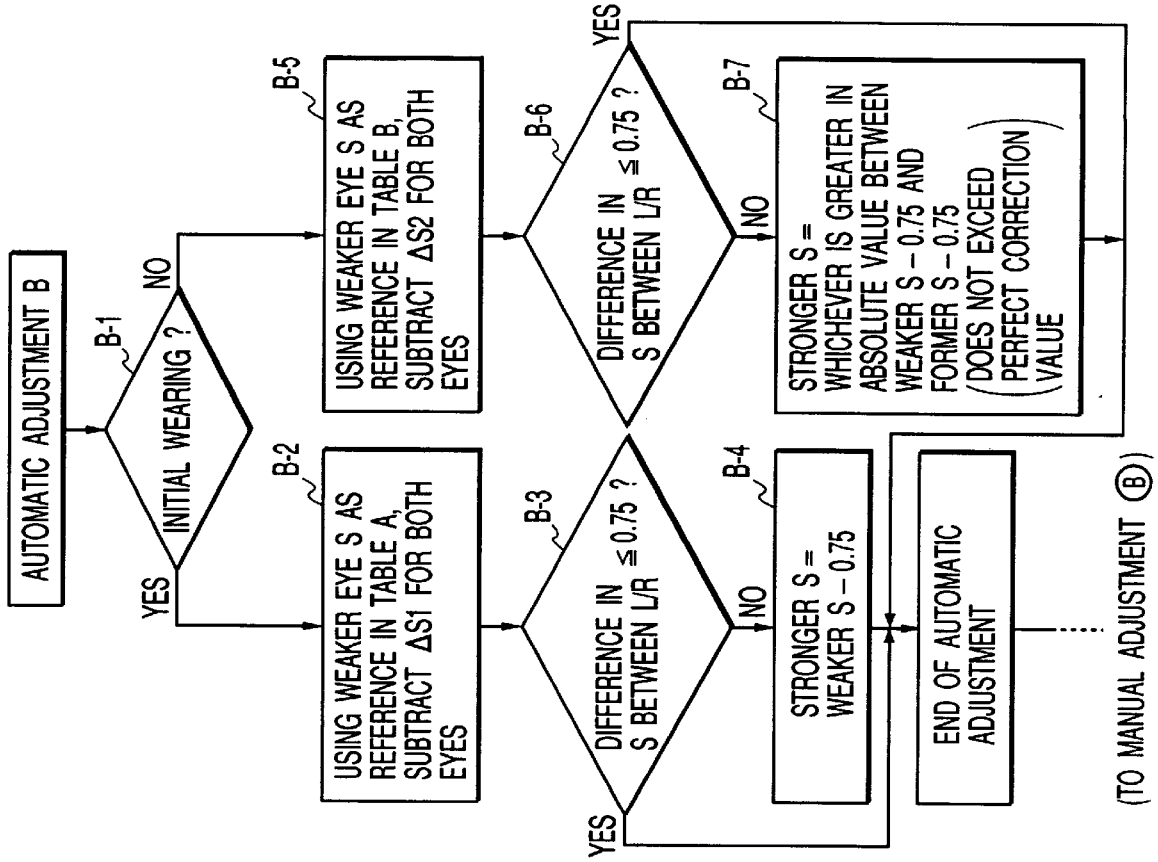
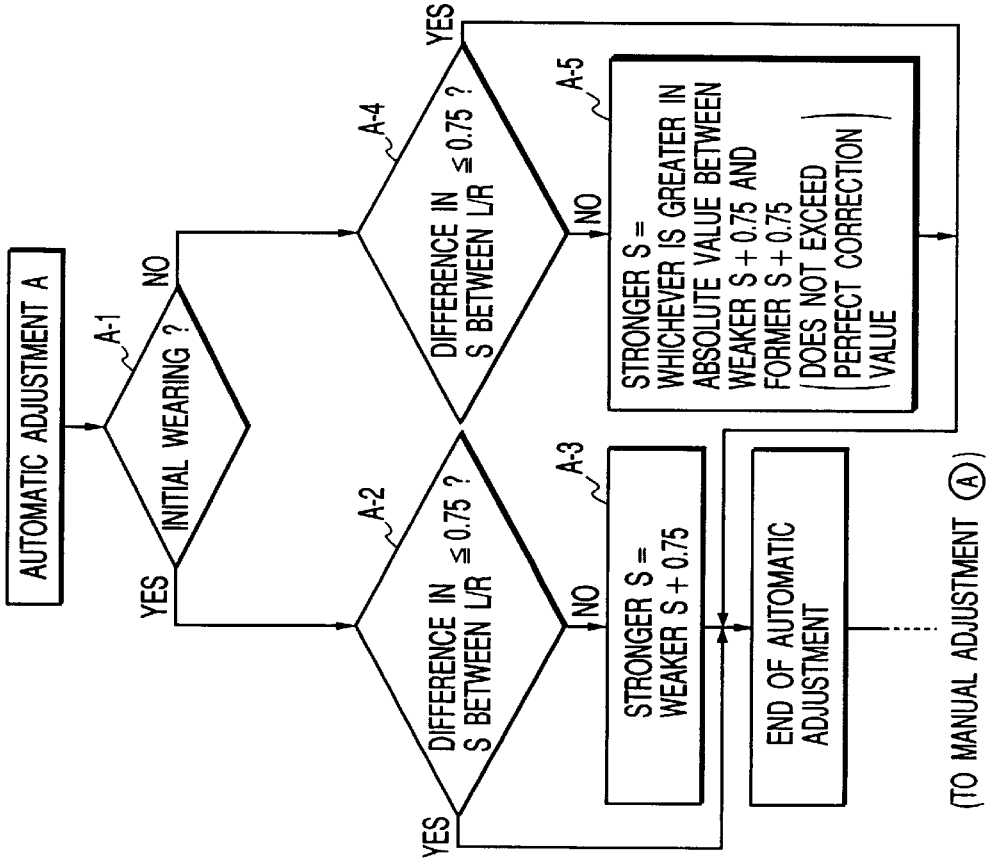

FIG. 14

TABLE A
(POWER ADJUSTMENT FOR MYOPIA [INITIAL WEARING])

| PERFECT CORRECTION S1 | CORRECTION AMOUNT ΔS1 |
|---|---|
| −0.25<br>−0.50<br>−0.75<br>−1.00<br>−1.25<br>−1.50<br>−1.75<br>−2.00<br>−2.25<br>−2.50<br>−2.75<br>−3.00<br>−3.25<br>−3.50<br>−3.75<br>−4.00<br>−4.25<br>−4.50<br>−4.75<br>−5.00<br>⋮ | S1/2<br>(HOWEVER, ROUNDED UP IN 0.25D STEPS) |

TABLE B
(POWER ADJUSTMENT FOR MYOPIA [2ND TIME OR MORE])

| DIFFERENCE BETWEEN FORMER SPECTACLES AND PERFECT CORRECTION S2 | CORRECTION AMOUNT ΔS2 |
|---|---|
| ⋮<br>+0.50<br>+0.25<br>0<br>−0.25<br>−0.50<br>−0.75<br>−1.00<br>−1.25<br>−1.50<br>−1.75<br>−2.00<br>−2.25<br>−2.50<br>−2.75<br>−3.00<br>⋮ | 0<br><br>S2/2<br>(HOWEVER, ROUNDED UP IN 0.25D STEPS)<br><br>S2+0.75 |

TABLE C
(POWER ADJUSTMENT FOR ASTIGMATISM [INITIAL WEARING])

| PERFECT CORRECTION C1 | CORRECTION AMOUNT ΔC1 |
|---|---|
| −0.25<br>−0.50<br>−0.75<br>−1.00<br>−1.25<br>−1.50<br>−1.75<br>−2.00<br>−2.25<br>−2.50<br>−2.75<br>−3.00<br>−3.25<br>−3.50<br>−3.75<br>⋮ | C1/2<br>(HOWEVER, ROUNDED UP IN 0.25D STEPS) |

TABLE D
(POWER ADJUSTMENT FOR ASTIGMATISM [2ND TIME OR MORE])

| DIFFERENCE BETWEEN FORMER SPECTACLES AND PERFECT CORRECTION C2 | CORRECTION AMOUNT ΔC2 |
|---|---|
| ⋮<br>+0.50<br>+0.25<br>0<br>−0.25<br>−0.50<br>−0.75<br>−1.00<br>−1.25<br>−1.50<br>−1.75<br>−2.00<br>−2.25<br>−2.50<br>−2.75<br>−3.00<br>−3.25<br>⋮ | 0<br><br>C2/2<br>(HOWEVER, ROUNDED UP IN 0.25D STEPS)<br><br>C2+0.75 |

FIG. 18

|  | UNAIDED | | FAR USE | |
|---|---|---|---|---|
|  | R BINOCULAR L | | | |
| SUBJECTIVE | | | | SUBJECTIVE |
| -2.75 | -2.75 | S | -2.75 | -3.00 |
| -1.25 | -1.25 | C | -0.75 | -0.75 |
| 175 | 175 | A | 5 | 5 |
| | DESIRED VISUAL ACUITY VALUE=1.0 | | | |
| 1.2 | | | | 1.0 |

EXECUTE

FIG. 19

| VISUAL ACUITY VALUE (VA1) OF PERFECT CORRECTION VALUE (POWER) | DESIRED VISUAL ACUITY VALUE (VA2) | POWER (D0) SUBTRACTED FROM PERFECT CORRECTION POWER |
|---|---|---|
| 2.0 | 2.0<br>1.5<br>1.2<br>1.0<br>0.9<br>0.8<br>0.7<br>0.6 | 0 (D)<br>-0.25<br>-0.50<br>-0.50<br>-0.75<br>-0.75<br>-1.00<br>-1.00 |
| 1.5 | 1.5<br>1.2<br>1.0<br>0.9<br>0.8<br>0.7<br>0.6 | 0<br>-0.25<br>-0.25<br>-0.50<br>-0.50<br>-0.75<br>-0.75 |
| 1.2 | 1.2<br>1.0<br>0.9<br>0.8<br>0.7<br>0.6 | 0<br>-0.25<br>-0.25<br>-0.50<br>-0.50<br>-0.75 |
| 1.0 | 1.0<br>0.9<br>0.8<br>0.7<br>0.6 | 0<br>-0.25<br>-0.25<br>-0.50<br>-0.50 |
| 0.9 | 0.9<br>0.8<br>0.7<br>0.6 | 0<br>-0.25<br>-0.25<br>-0.50 |
| 0.8 | 0.8<br>0.7<br>0.6 | 0<br>-0.25<br>-0.25 |
| 0.7 | 0.7<br>0.6 | 0<br>-0.25 |

OPTOMETRIC APPARATUS

BACKGROUND OF THE INVENTION

The present invention relates to an optometric apparatus suitable for obtaining a correction power for correcting the refractive power of an eye to be examined.

When prescribing a spectacle lens or the like for correcting the refractive power of an eye to be examined, after determining a perfect correction power to allow maximum visual acuity to be obtained, a power suitable for wearing is prescribed by taking into consideration the power of a former spectacle which was formerly used by a subject.

In deriving appropriate prescription powers, much depends on an examiner's optometric knowledge or experience, it is not easy for an inexperienced examiner to do so. Accordingly, apparatuses have been proposed which are adapted to estimate prescription powers which are considered to be appropriate for the subject on the basis of perfect correction powers and adjustment factors for adjusting correction powers.

However, the method of determining prescription powers differs depending on examiners, spectacle shops, their localities, racial features, and the like. Accordingly, even if prescription powers which are estimated to be optimally suited are obtained as described above, the examiner makes fine adjustment of the powers and finally determines prescription powers. It takes time in the fine adjustment in a case where there is a large discrepancy between the prescription powers obtained by the apparatus and the prescription preferred by the examiner.

Further, astigmatism makes it difficult to determine the prescription powers. That is, astigmatism is not necessary identical for the far use and the near use. To appropriately effect the correction of the eye to be examined, a correction method needs to be changed depending on whether the astigmatism is oblique astigmatism, astigmatism with the rule, or astigmatism against the rule. It is even more difficult to do so in the case of an examiner lacking in optometric knowledge or an inexperienced examiner.

Moreover, there is another requirement which hardly be accomplished by an examiner lacking in optometric knowledge or an inexperienced examiner. In prescribing a power suitable for wearing by taking into consideration the power of a former spectacle which was formerly used by a subject, the prescription powers are generally determined by placing emphasis on the alleviation of the uneasy sensation rather than on the appearance since if the prescription power is suddenly made strong in comparison to the former one, the subject finds it difficult to become accustomed to the lens and often feels an uneasy sensation.

However, although there are some subjects who desire to secure up to visual acuity values by any means (e.g., at the time of acquisition or renewal of a driver's license), in the case of powers which are determined to alleviate the uneasy sensation, there are cases where the prescriptions fail to satisfy their desires. It is not easy for an examiner lacking in optometric knowledge or an inexperienced examiner to derive powers for securing the visual acuity values desired by the subject.

In addition, in a case where the prescription value exceeds the desired visual acuity value, a high visual acuity value is not especially needed in some cases.

SUMMARY OF THE INVENTION

In view of these problems, it is an object of the present invention to provide an optometric apparatus capable of effecting the examination efficiently by reducing the amount of power adjustment by the examiner.

It is another object of the present invention to provide an optometric apparatus capable of obtaining an appropriate prescription power for an astigmatic eye.

It is yet another object of the present invention is to provide an optometric apparatus which can be easily operated by an examiner lacking in optometric knowledge or by an inexperienced examiner.

It is still another object of the present invention to provide an optometric apparatus capable of making it possible to easily obtain the correction power in a state desired by the subject and improve the examination efficiency.

The present invention provides an optometric apparatus described below.

(1) An optometric apparatus for obtaining a correction power correcting ametropia based on a refractive power of a subject eye, the apparatus comprising:

data input means for inputting a perfect correction power of a subject eye and adjustment factor data for adjusting the correction power;

program storing means for storing a program used for estimating a prescription power by making adjustments to the correction power in relation to the perfect correction power on the basis of the adjustment factor data inputted by the input means, the program including a step of obtaining a correction amount used in making adjustments to the correction power;

data storing means for storing a multiplicity of actual prescription powers, and perfect correction powers and adjustment factor data on the basis of which an examiner determined the actual prescription power in the past, respectively;

first calculating means for obtaining a variable coefficient for making variable the correction amount in the program by statistically processing a multiplicity of data stored in the data storing means;

program advancing means for advancing the program;

second calculating means for determining an estimated prescription power in accordance with the program and on the basis of the variable correction amount obtained by the first calculating means; and display means for displaying the estimated prescription power determined by the second calculating means.

(2) An optometric apparatus according to (1), wherein the data input means input the perfect correction power of the subject eye, a visual acuity value of the subject eye when its power is corrected to the perfect correction power, and a desired visual acuity value sdesired by a subject for the subject eye, wherein the program further includes a step of estimating a prescription power by making adjustments to the correction power to secure the desired visual acuity value on the basis of the perfect correction power, the visual acuity value and the desired visual acuity value inputted by the data input means, and wherein the program advancing means include selecting means for selecting whether or not the step of estimating a prescription power by making adjustments to the correction power to secure the desired visual acuity value is executed.

(3) An optometric apparatus according to (2), wherein the data input means further input a power of a former spectacle and a visual acuity value obtained when the subject wears the former spectacle, and wherein the step of estimating a prescription power by making adjustments to the correction power to secure the desired visual acuity value estimates the prescription power by making adjustments to the correction power to secure the desired visual acuity value on the basis of the perfect correction power of the subject eye, the visual acuity value of the subject eye when its power is corrected to the perfect correction power, the desired visual acuity value desired by a subject for the subject eye, the power of the former spectacle and the visual acuity value obtained when the subject wears the former spectacle.

(4) An optometric apparatus according to (1), further comprising:

correction-amount storing means for storing as a correction table the correction amount used in making adjustments to the correction power, and wherein the program estimates the prescription power by making adjustments to the correction power with the correction amount obtained from the correction table.

(5) An optometric apparatus according to (1), wherein the program further includes a step of obtaining one of different adjustment powers depending on whether a kind of astigmatism of the perfect correction power is oblique astigmatism, astigmatism with the rule, or astigmatism against the rule.

(6) An optometric apparatus according to (5), wherein the program further includes a step of setting the adjustment power as the perfect correction power of astigmatism if the kind of astigmatism is astigmatism against the rule.

(7) An optometric apparatus according to (5), wherein the program further includes a step of setting the adjustment power to a power which is closer to the perfect correction power than the adjustment power for the astigmatism with the rule is if the kind of astigmatism is astigmatism against the rule.

(8) An optometric apparatus for obtaining a correction power correcting ametropia based on a refractive power of a subject eye, the apparatus comprising:

data input means for inputting a perfect correction power of a subject eye and adjustment factor data for adjusting the correction power;

program storing means for storing a program used for estimating a prescription power by making adjustments to the correction power in relation to the perfect correction power on the basis of the adjustment factor data inputted by the input means, the program including a step of obtaining one of different adjustment powers depending on whether a kind of astigmatism of the perfect correction power is oblique astigmatism, astigmatism with the rule, or astigmatism against the rule;

program advancing means for advancing the program;

prescription-power calculating means for determining an estimated prescription power in accordance with the program; and display means for displaying the estimated prescription power determined by the prescription-power calculating means.

(9) An optometric apparatus according to (8), wherein the program further includes a step of setting the adjustment power as the perfect correction power of astigmatism if the kind of astigmatism is astigmatism against the rule.

(10) An optometric apparatus according to (8), wherein the program further includes a step of setting the adjustment power to a power which is closer to the perfect correction power than the adjustment power for the astigmatism with the rule is if the kind of astigmatism is astigmatism against the rule.

(11) An optometric apparatus for obtaining a correction power correcting ametropia based on a refractive power of a subject eye, the apparatus comprising:

perfect-correction-value input means for inputting a perfect correction power of a subject eye and a visual acuity value of the subject eye when its power is corrected to the perfect correction power;

desired-visual-acuity-value input means for inputting a desired visual acuity value desired by a subject for the subject eye;

program storing means for storing a program used for estimating a prescription power, the program including a first step of estimating the prescription power by making adjustments to the correction power to secure the desired visual acuity value on the basis of the perfect correction power, the visual acuity value and the desired visual acuity value inputted by both the input means;

program advancing means for advancing the program;

prescription-power calculating means for determining an estimated prescription power in accordance with the program; and display means for displaying the estimated prescription power determined by the prescription-power calculating means.

(12) An optometric apparatus according to (11), further comprising:

former-spectacle-value input means for inputting a power of a former spectacle and a visual acuity value obtained when the subject wears the former spectacle, wherein the first step estimates the prescription power by making adjustments to the correction power to secure the desired visual acuity value on the basis of the perfect correction power of the subject eye, the visual acuity value of the subject eye when its power is corrected to the perfect correction power, the desired visual acuity value desired by a subject for the subject eye, the power of the former spectacle and the visual acuity value obtained when the subject wears the former spectacle.

(13) An optometric apparatus according to (11), further comprising:

correction-amount storing means for storing as a correction table an correction amount used in making adjustments to the correction power, and wherein the first step estimates the prescription power by making adjustments to the correction power with the correction amount obtained from the correction table.

(14). An optometric apparatus according to (11), further comprising:

data input means for inputting adjustment factor data for adjusting the correction power, wherein the program includes a second step of estimating a prescription power by making adjustments to the correction power in relation to the perfect correction power on the basis of the adjustment factor data inputted by the input means, and wherein the program advancing means includes selecting means for selectively executing either one of the first and second steps.

5

Figure 2:
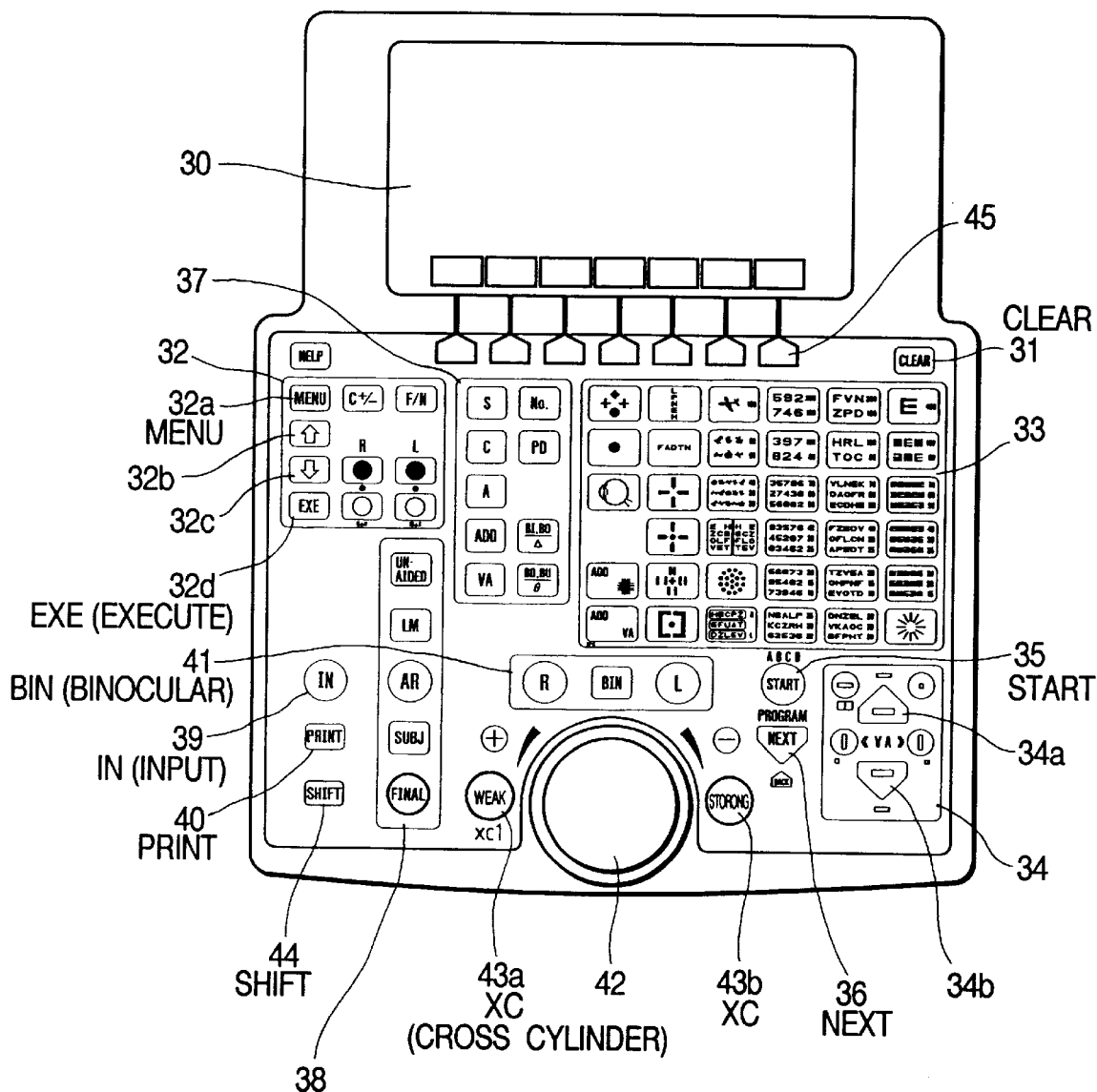
Figure 3:
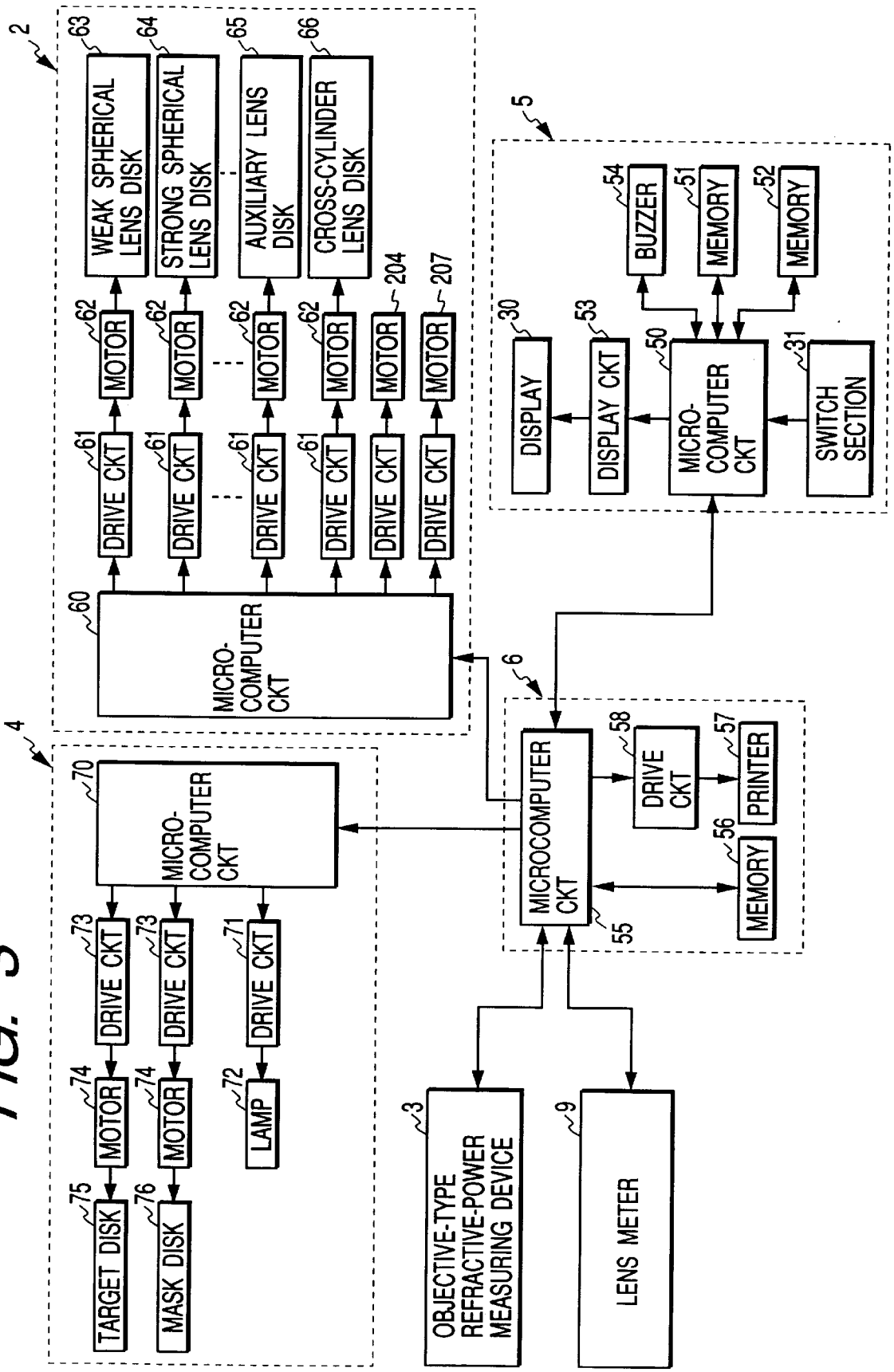
Figure 4:
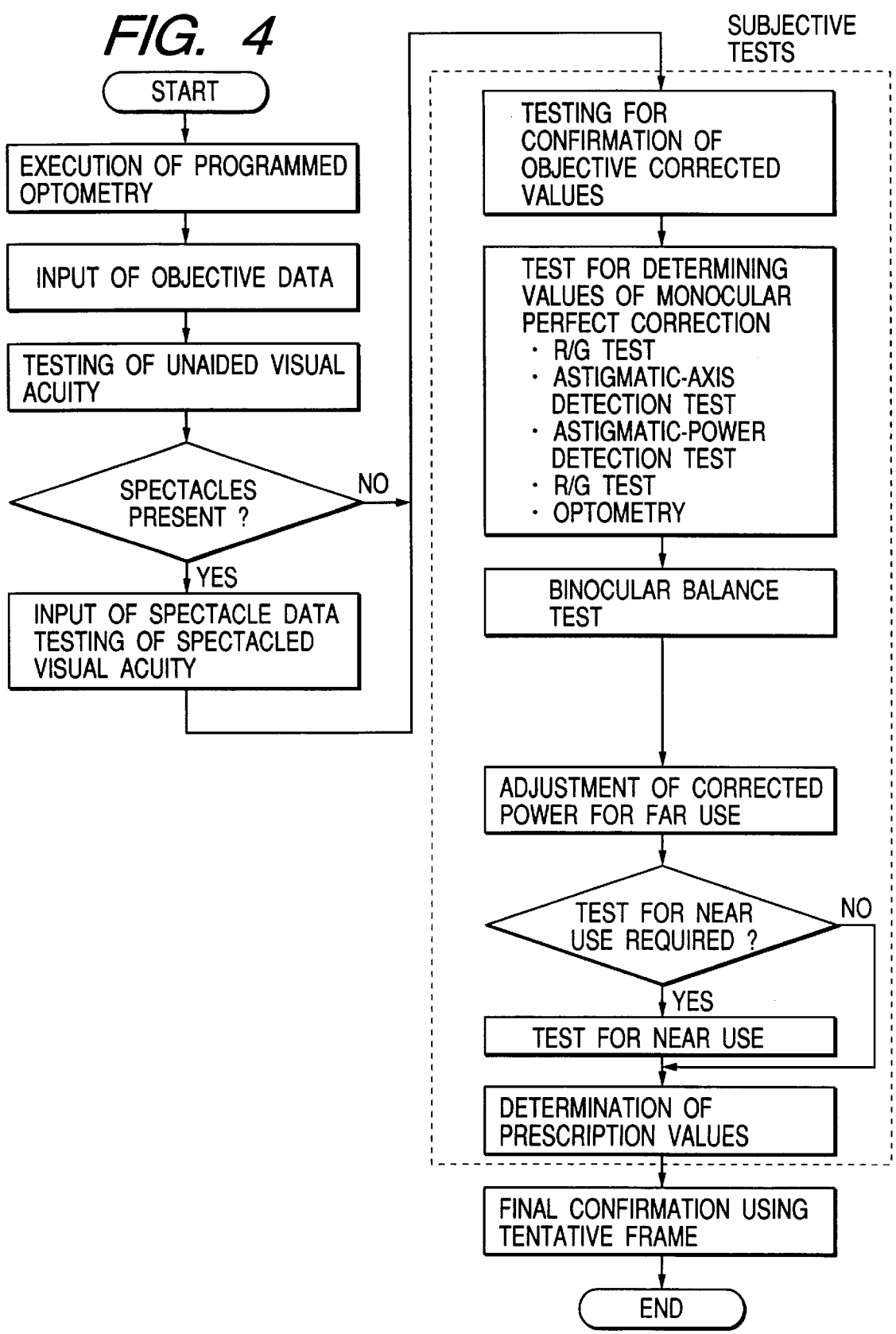
Figures 5, 6:
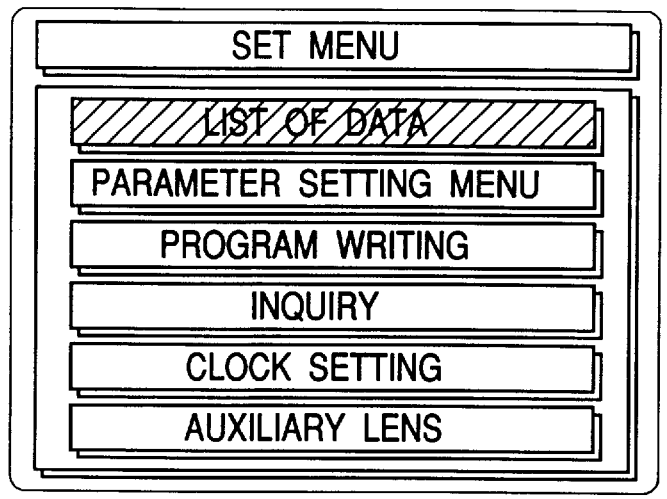
Figure 7:
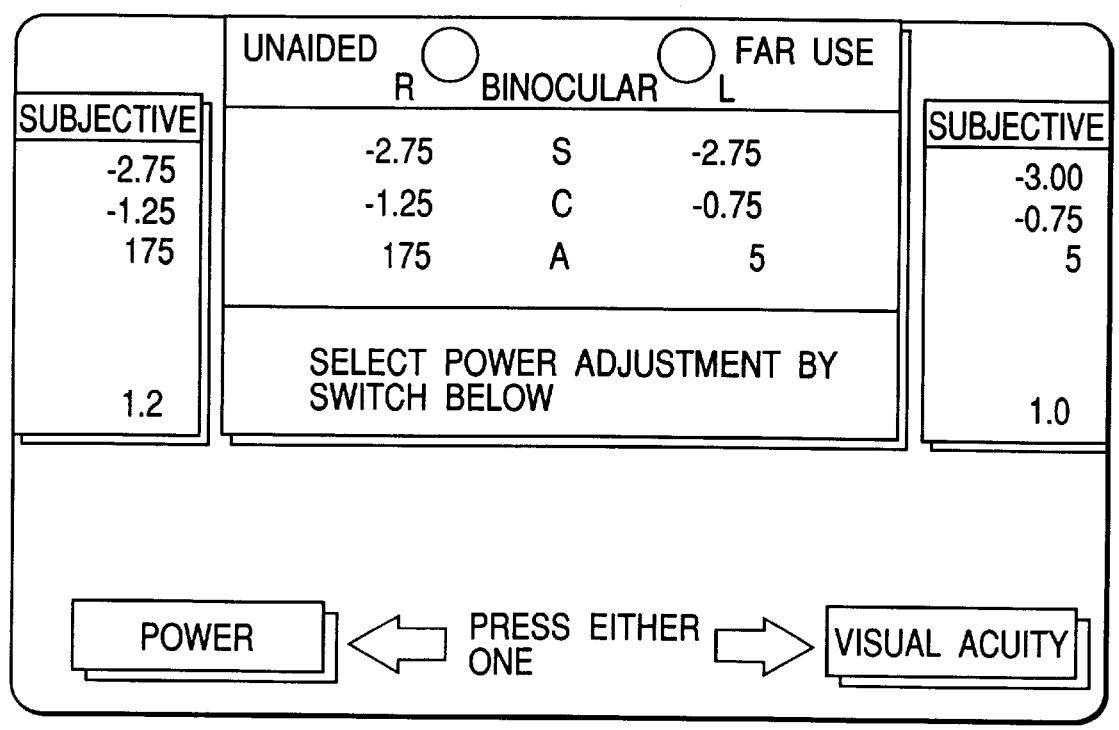
Figure 8:
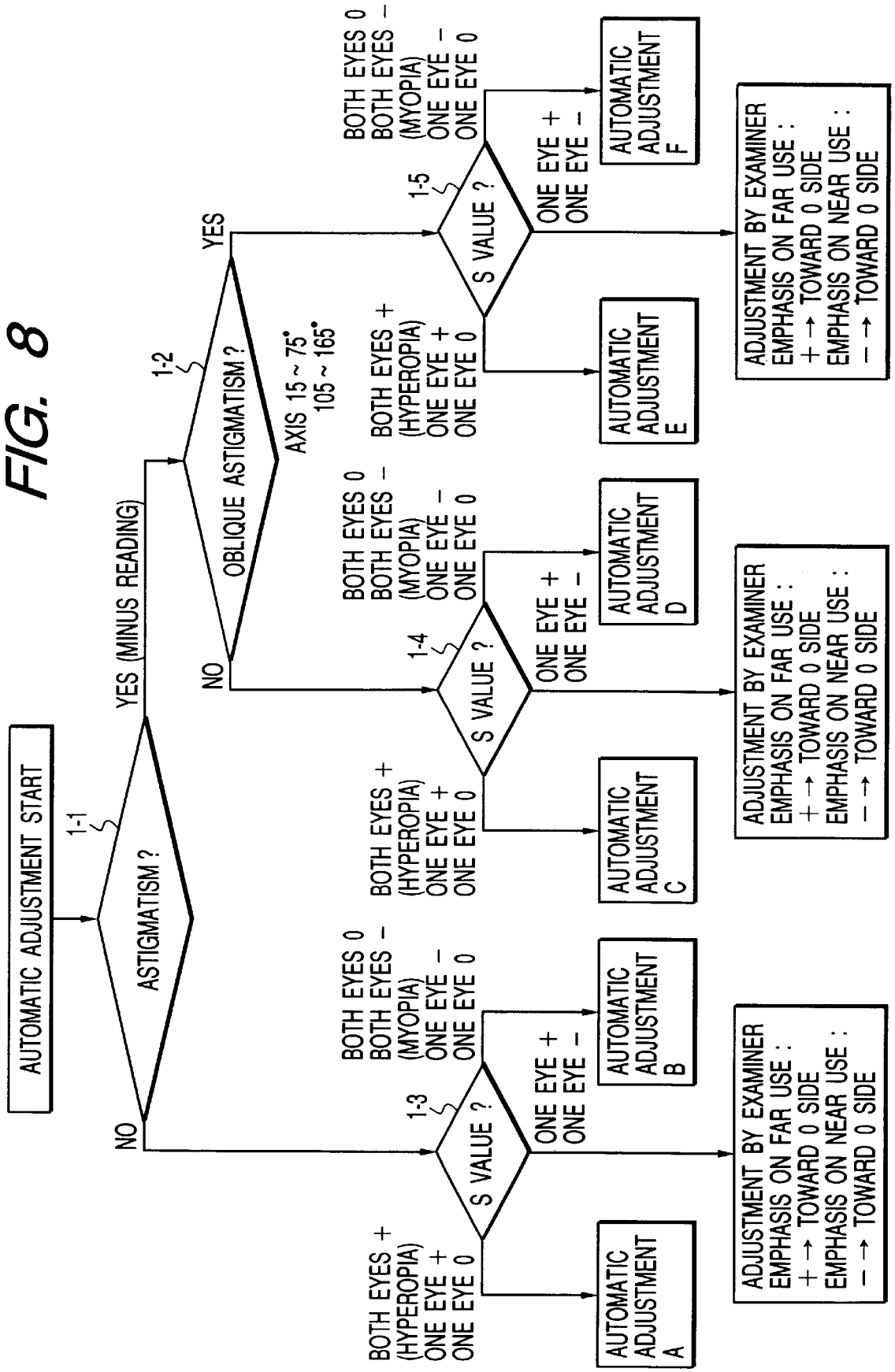
Figure 10:
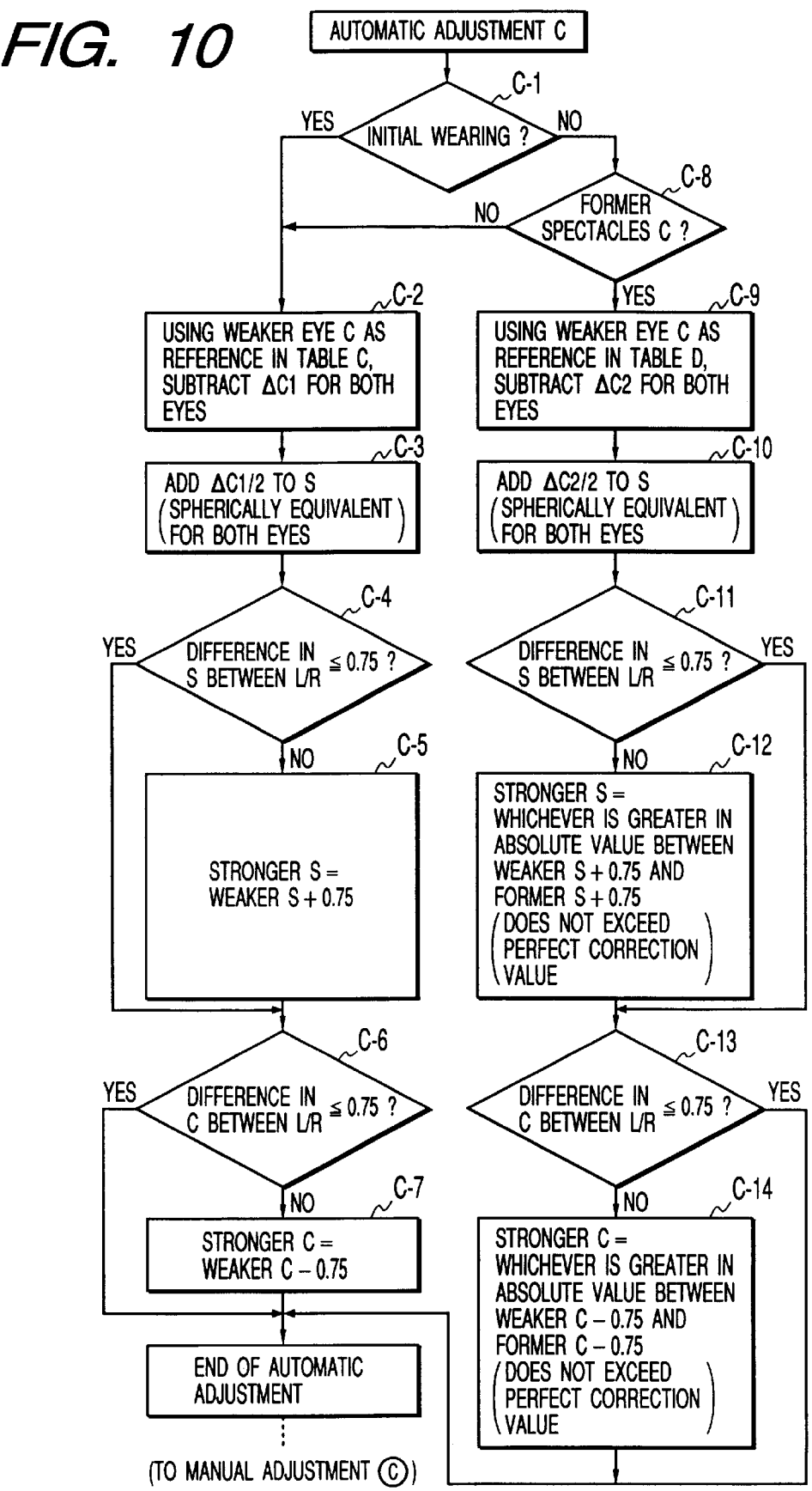
Figure 11:
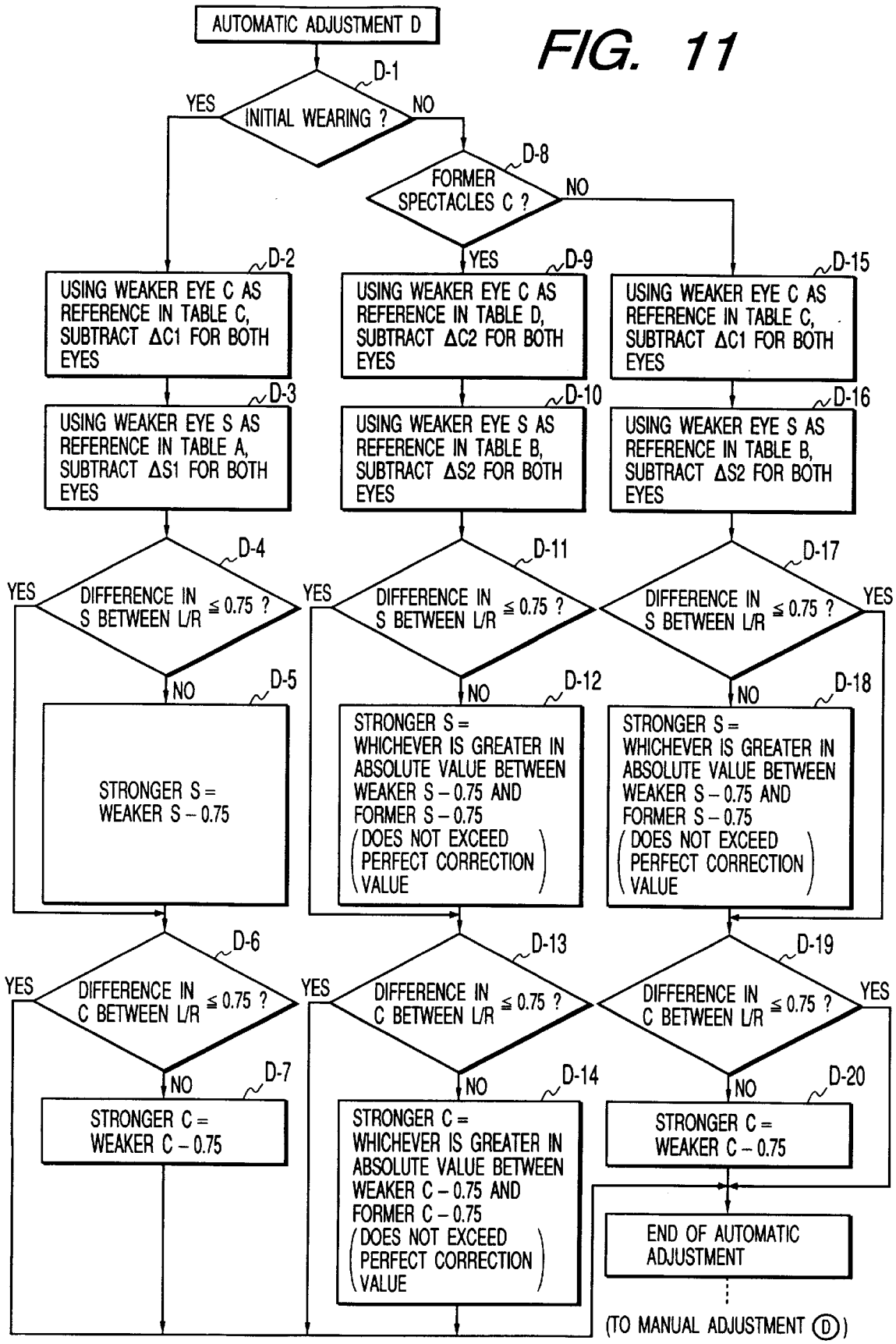
Figure 12:
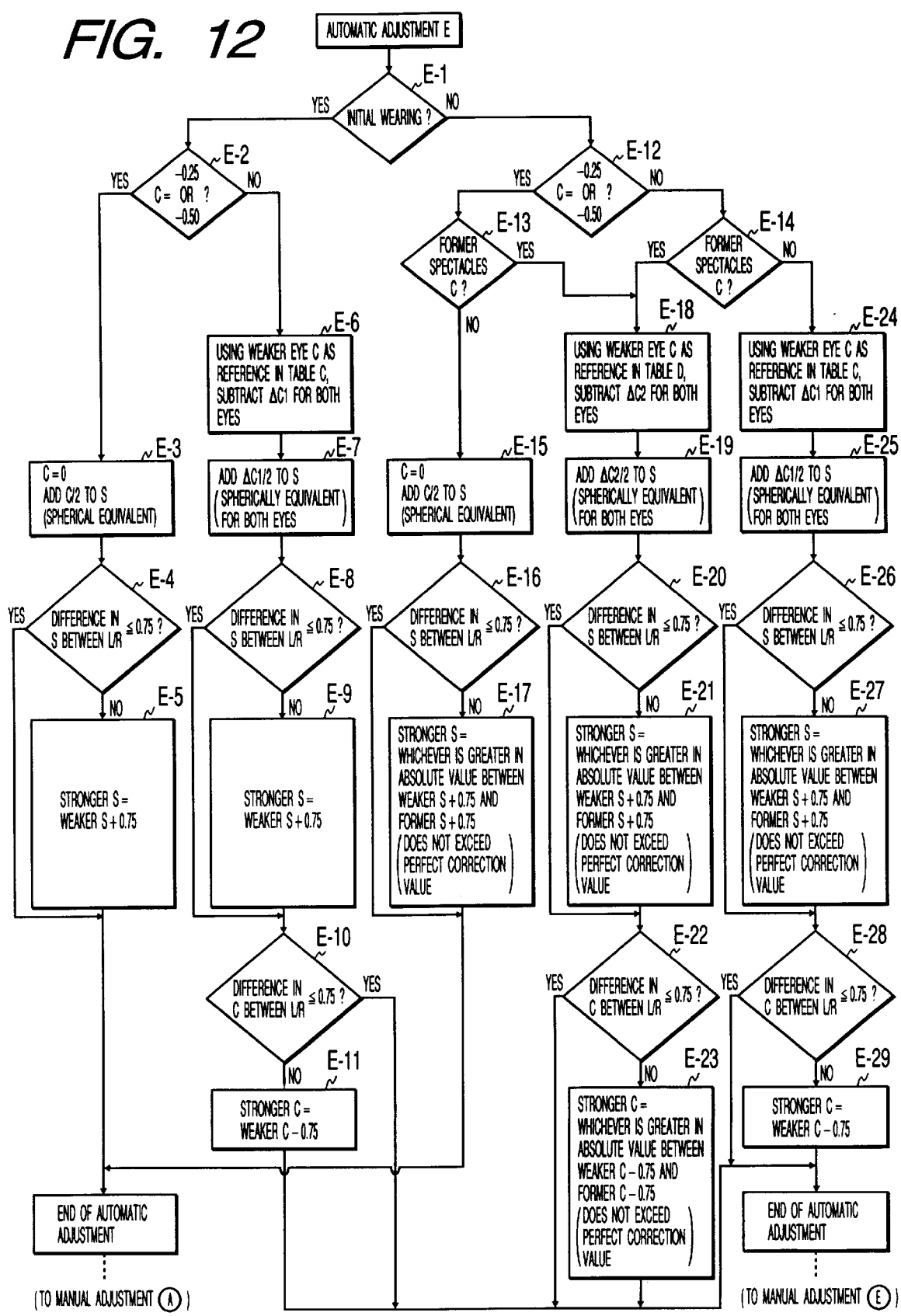
Figure 13:
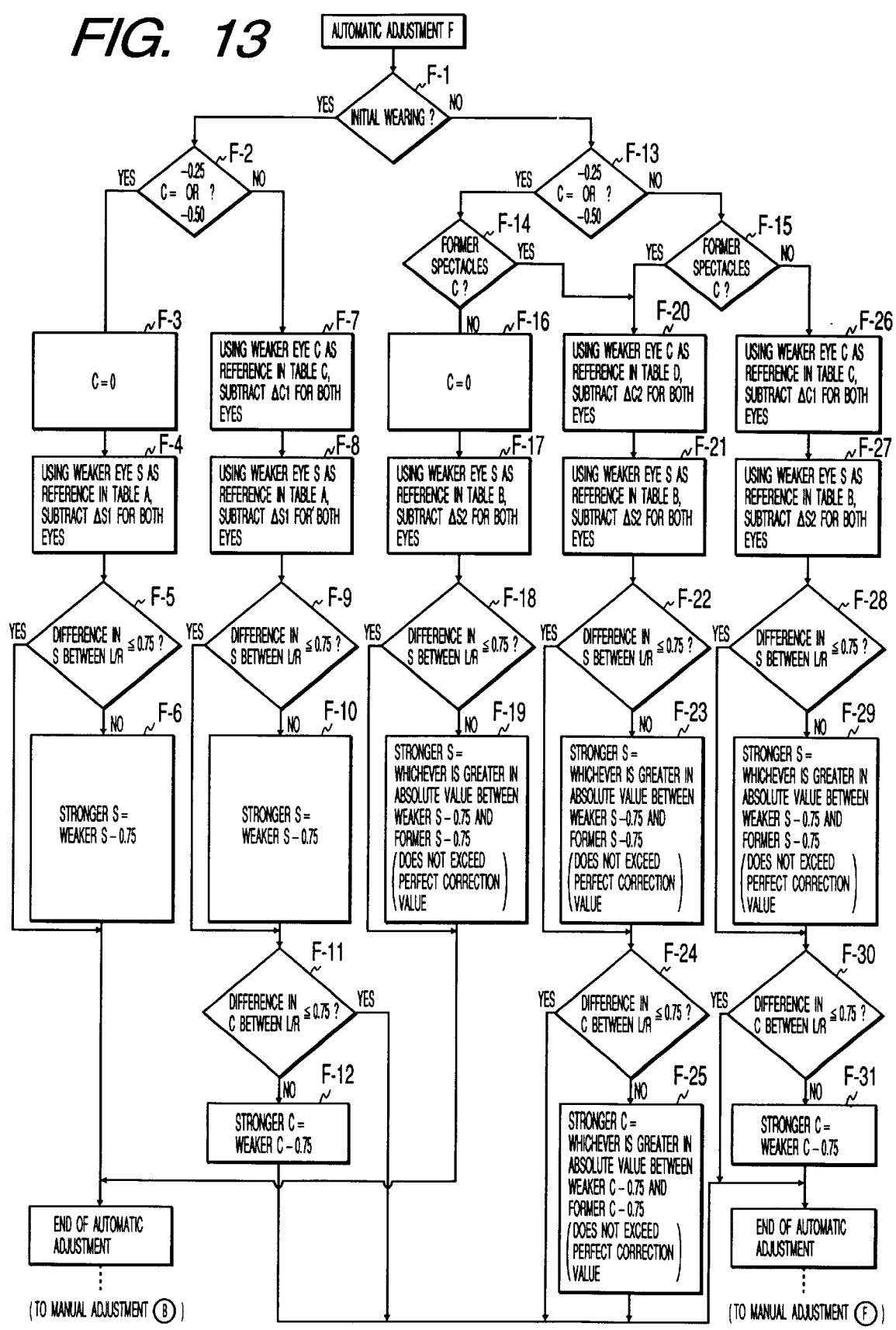
Figure 15:
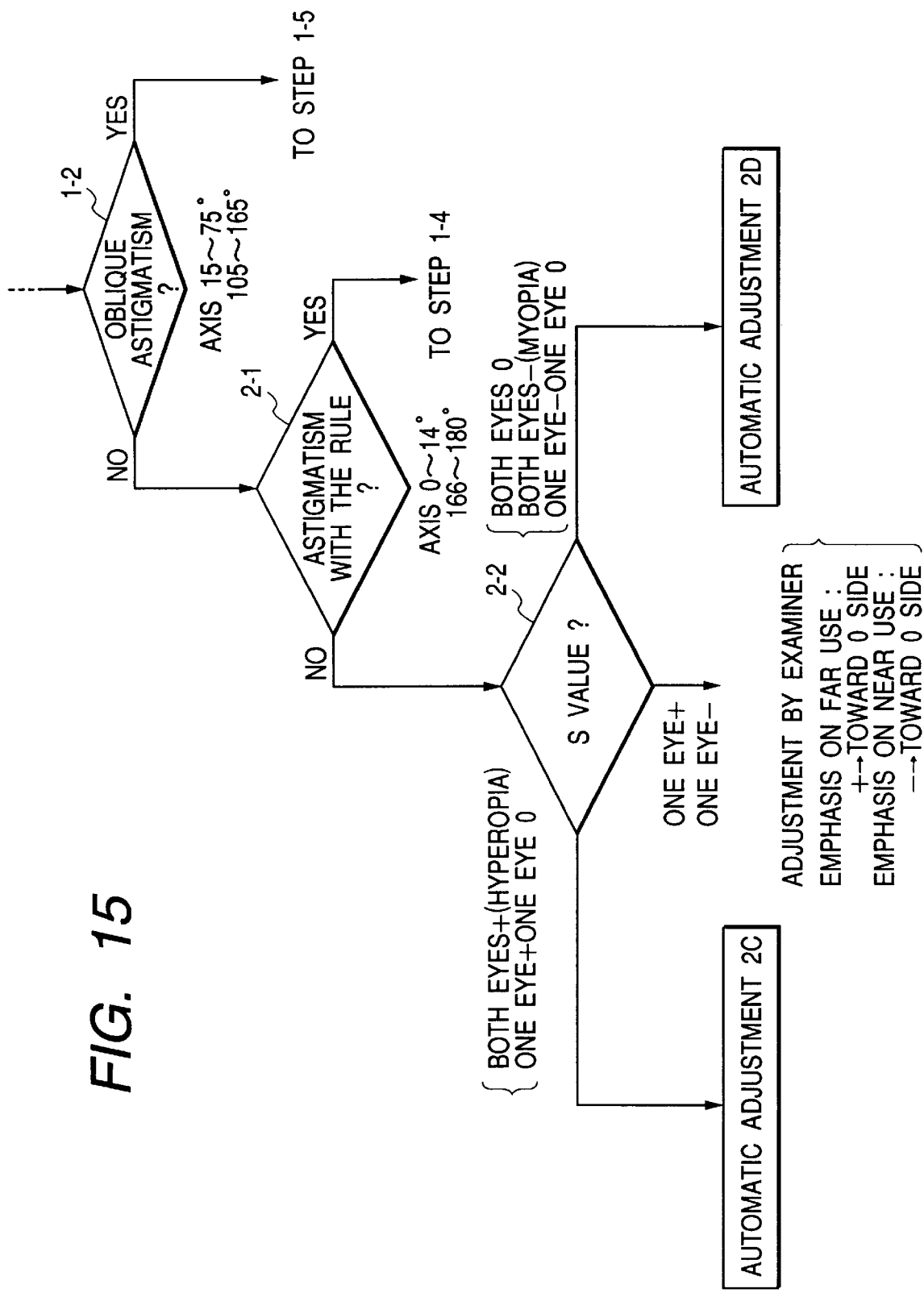
Figure 16:
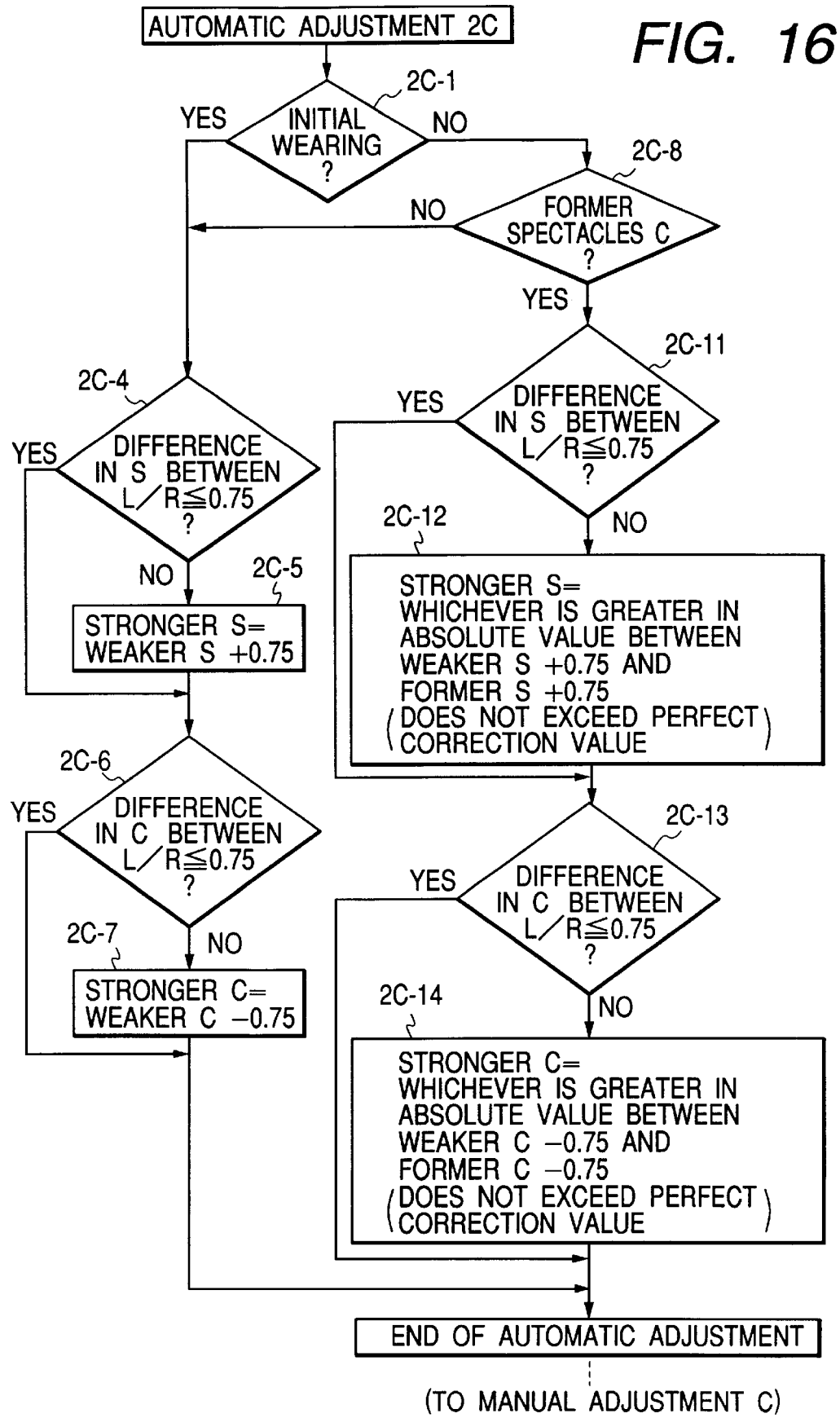
Figure 17:
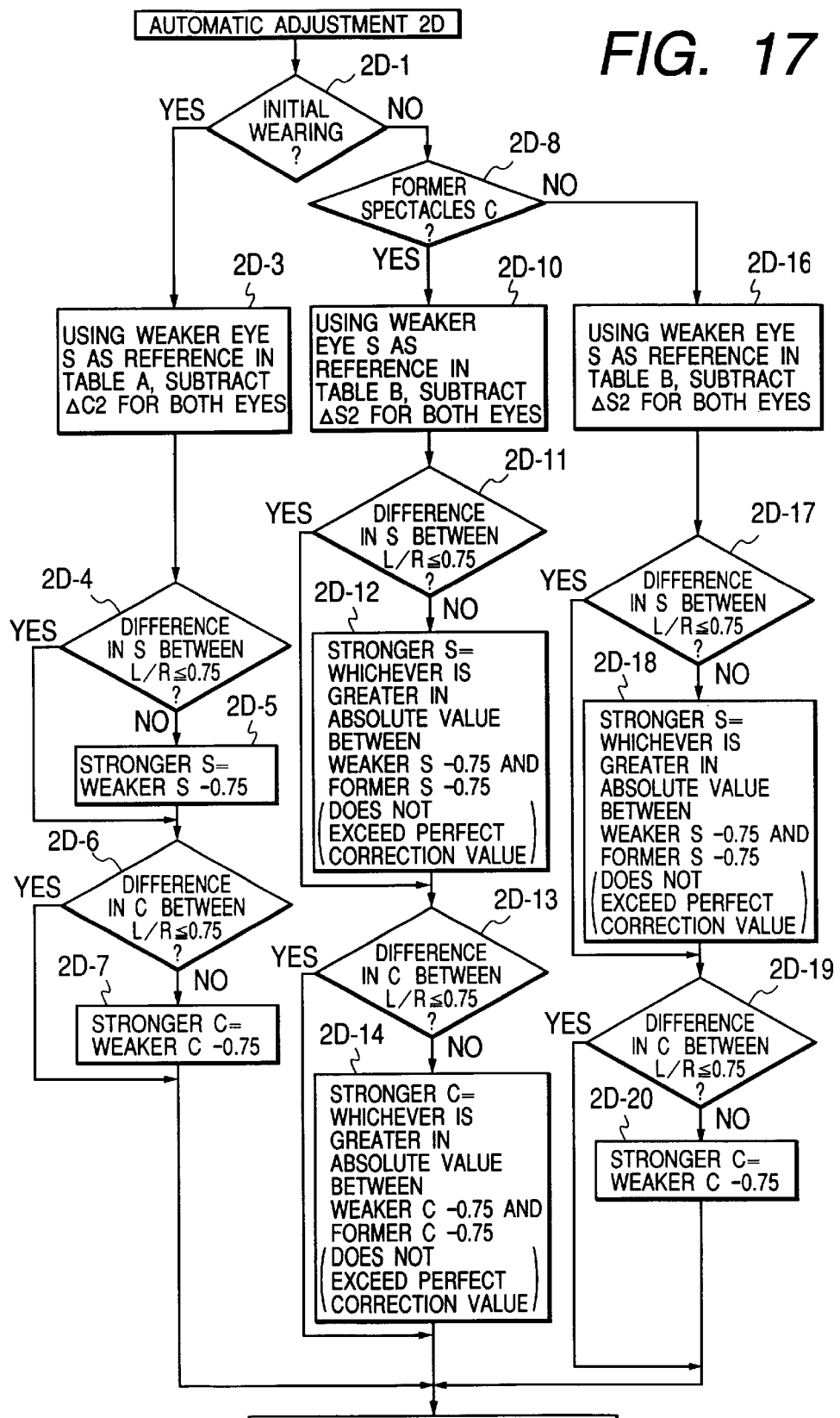
Figure 20:
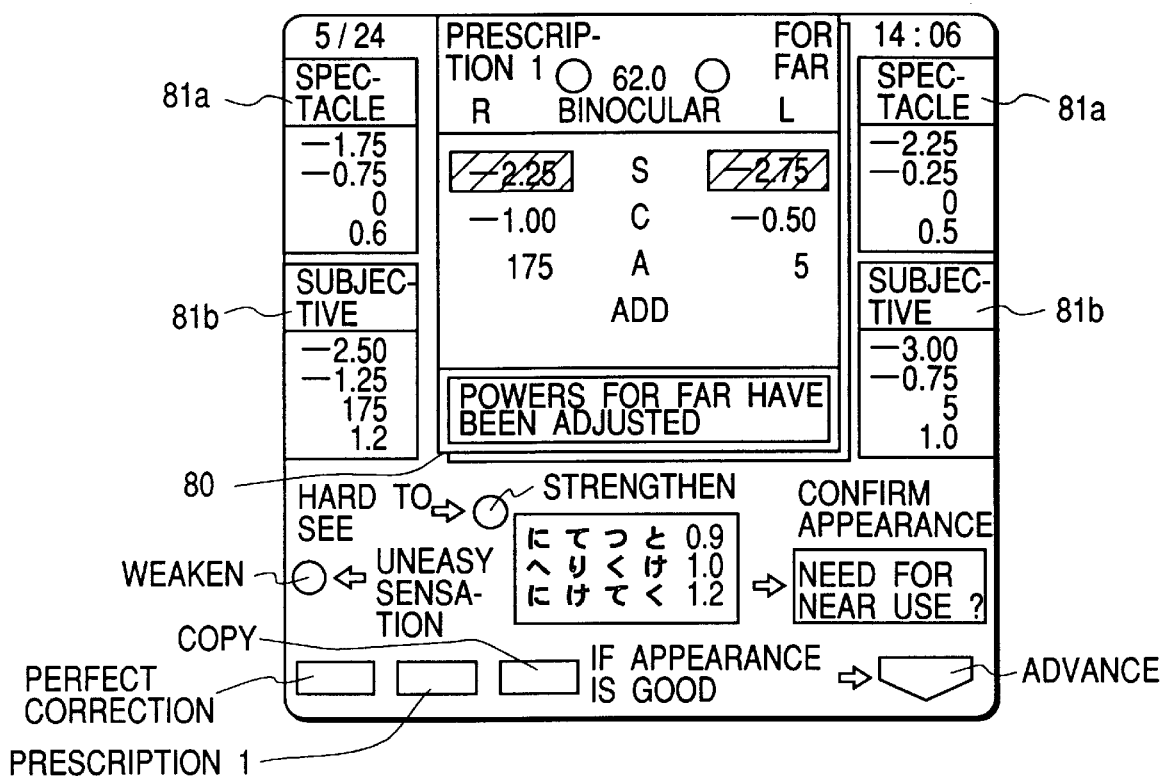
Figure 21:
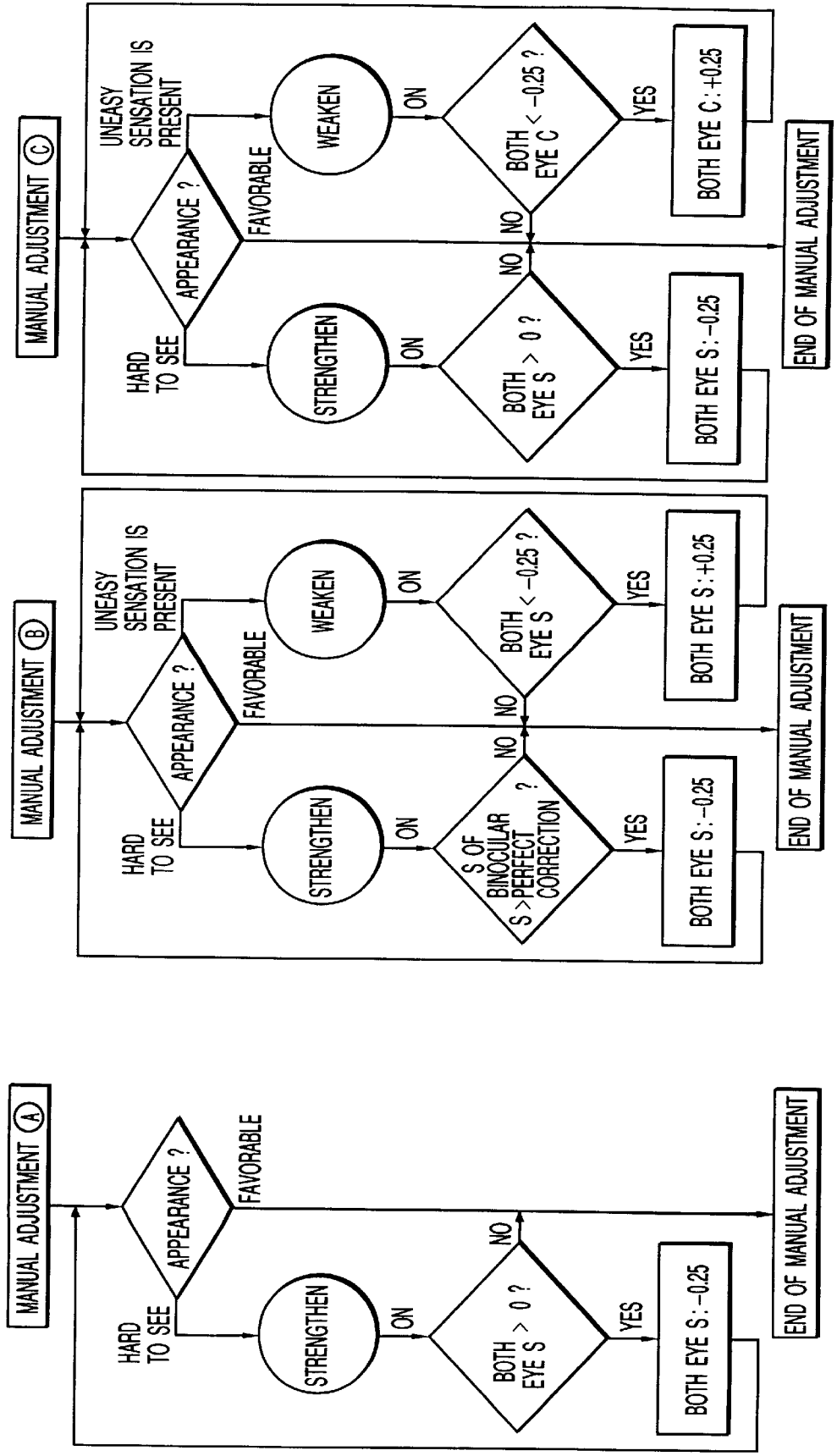

FIG. 2 is a top view of a controller;

FIG. 3 is a diagram illustrating the control of the apparatus in accordance with the embodiment;

FIG. 4 is a diagram illustrating a flowchart of an optometric program in accordance with the embodiment;

FIG. 5 is a diagram illustrating an example of a menu screen for setting which is displayed on a display;

FIG. 6 is a diagram illustrating an example of the screen at the time of starting the testing of unaided visual acuity;

FIG. 7 is a diagram illustrating an example of the menu screen for selecting which automatic adjustment program is be used;

FIG. 8 is a flowchart illustrating an automatic adjustment program with priority on powers;

FIG. 9 is a flowchart illustrating the automatic adjustment program with priority on powers;

FIG. 10 is a flowchart illustrating the automatic adjustment program with priority on powers;

FIG. 11 is a flowchart illustrating the automatic adjustment program with priority on powers;

FIG. 12 is a flowchart illustrating the automatic adjustment program with priority on powers;

FIG. 13 is a flowchart illustrating the automatic adjustment program with priority on powers;

FIG. 14 is a diagram illustrating calculation using Tables A to D for obtaining a correction amount for adjusting the correction power;

FIG. 15 is a diagram illustrating a power adjustment program in which cases of astigmatism with the rule and astigmatism against the rule are taken into consideration;

FIG. 16 is a diagram illustrating the power adjustment program in which cases of astigmatism with the rule and astigmatism against the rule are taken into consideration;

FIG. 17 is a diagram illustrating the power adjustment program in which cases of astigmatism with the rule and astigmatism against the rule are taken into consideration;

FIG. 18 is a diagram illustrating an example of the screen for inputting desired visual acuity values in a case where an automatic adjustment program with priority on visual acuity values has been selected;

FIG. 19 is a diagram illustrating an example of a table used in the calculation of powers with respect to desired visual acuity values;

FIG. 20 is a diagram illustrating an example of the display screen after automatic adjustment;

FIG. 21 is a diagram illustrating a control program for manual adjustment; and

Figure 22:
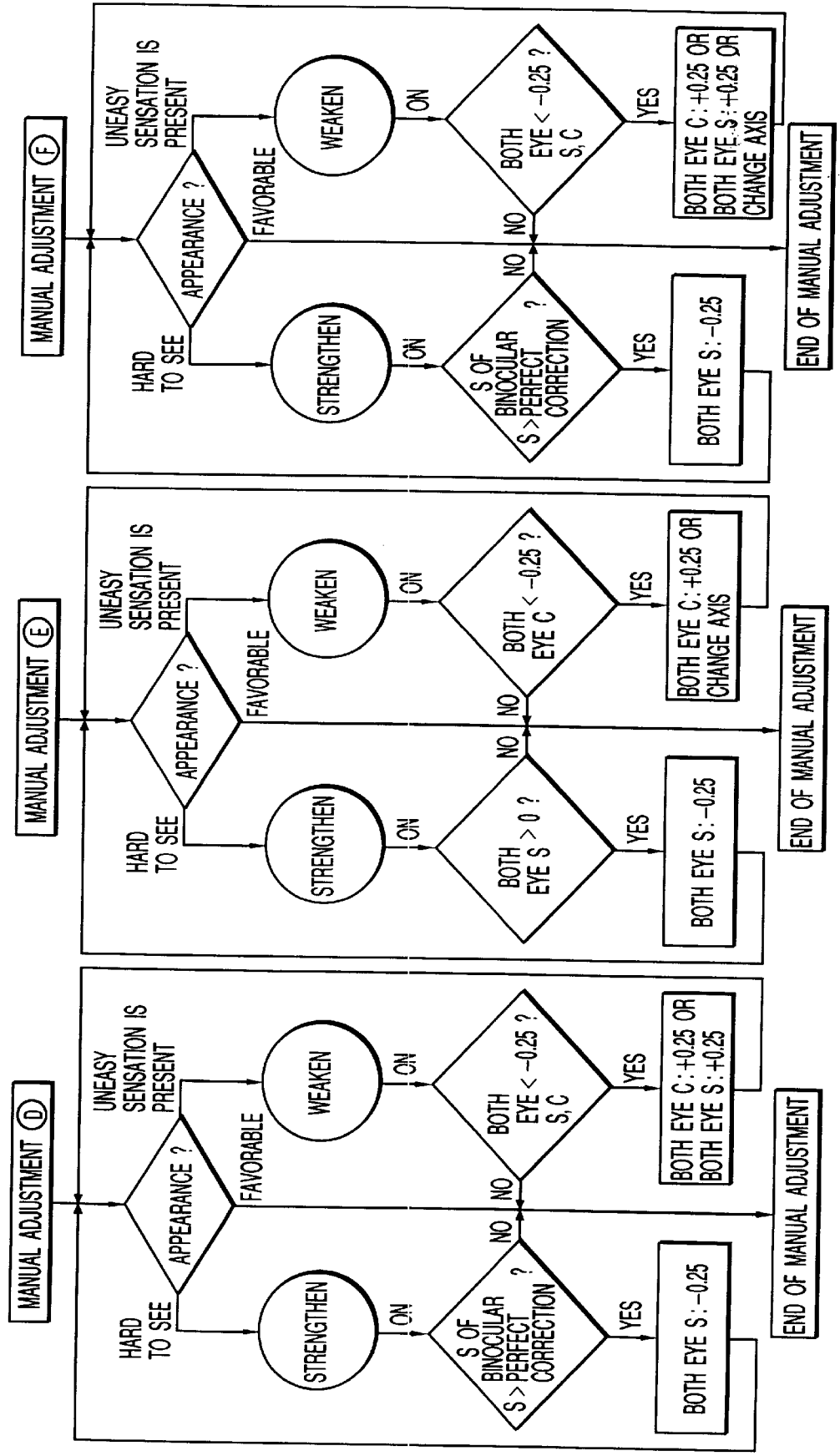

FIG. 22 is a diagram illustrating the control program for manual adjustment.

DETAILED DESCRIPTION OF THE PREFERRED EMBODIMENT

Figure 1:
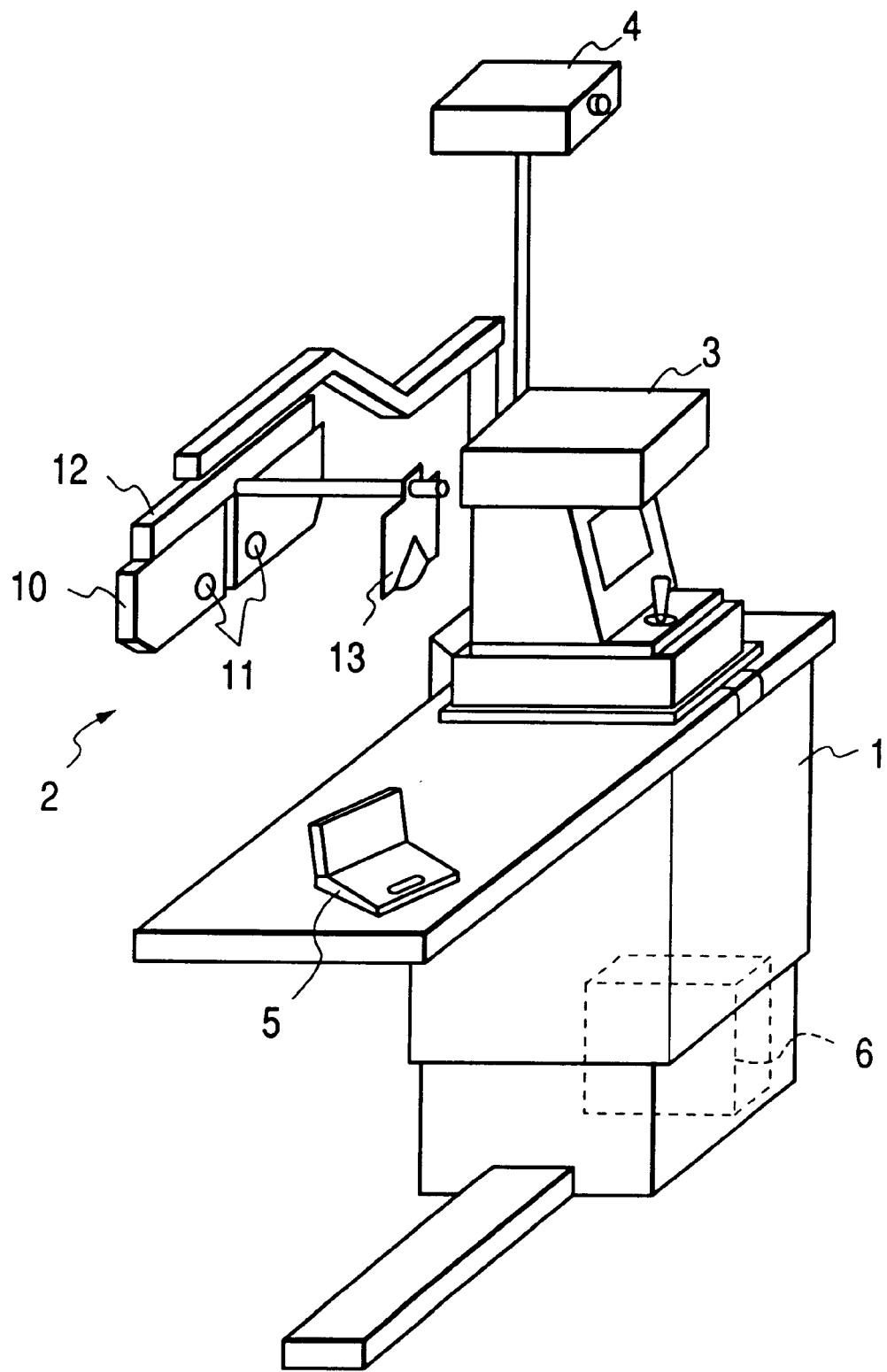
FIG. 1 is an external view illustrating an overall configuration of an optometric apparatus in accordance with an embodiment.

Referring now to the drawings, a description will be given of an embodiment of the present invention. FIG. 1 is an external view illustrating an overall configuration of an optometric apparatus in accordance with the embodiment.

Reference numeral 1 denotes an examination table disposed between a subject and an examiner, and reference numeral 2 denotes a subjective-type refractive-power measuring device. The subjective-type refractive-power measuring device 2 is provided with a pair of left and right lens units 10 in which various optical elements are electrically driven so as to be selectively disposed in a pair of test windows 11, as well as a suspending portion 12 for suspending the left and right lens units 10. Numeral 13 denotes a visual test chart for near use which is held by a near-point rod attached to the suspending portion 12 (this visual test chart 13 is removed from the front of the eyes during an examination for far use).

Numeral 3 denotes an objective-type refractive-power measuring device for measuring the refractive power of the eye by projecting a measuring target onto the fundus of the subject eye and detecting a projected image of the target on the fundus by means of a photo-detector. The objective-type refractive-power measuring device 3 is placed on a moving tray which is slidable on the examination table 1, and during an objective examination the objective-type refractive-power measuring device 3 is slid to a central position on the examination table 1 to execute measurement.

Numeral 4 denotes a projection-type target (chart) presenting device for presenting test targets (charts). Numeral 5 denotes a controller for operating the subjective-type refractive-power measuring device 2 and the projection-type target (chart) presenting device 4, and numeral 6 denotes a relay unit for relaying communication between the respective devices. A lens meter is also connected to the relay unit 6.

FIG. 2 is a top view of the controller 5. Reference numeral 30 denotes a liquid-crystal display which displays optometric information. Numeral 31 denotes a switch section which is provided with the following switches: a group of setting changeover switches 32 having switches which are used when changing over a display screen to a menu screen of the display 30 and effecting such as the setting of parameters; a group of target (chart) switches 33 for changing over a target (chart) to be presented from the target (chart) presenting device 4; a group of mask switches 34 for applying a mask necessary for the presented target (chart); a start switch 35 for executing programmed optometry; an advance switch 36 for advancing the item of programmed optometry to an ensuing item; a group of mode-change designating switches 37 for designating a mode of such as measurement data to be changed; a group of input-data designating switches 38 for designating a mode for entering data or a mode for measurement; a data input switch 39 which is used when data from the objective-type refractive-power measuring device, a lens meter, and the like are inputted; a print switch 40; a measurement-eye designating switch 41; and a dial switch 42 which is used when changing measurement values and inputting numerical values.

Reference numerals 43a and 43b denote changeover switches for changing over a cross-cylinder, and these changeover switches 43a and 43b are also used during adjustment of appearances in the stage of prescription. Numeral 44 denotes a shift switch, and if another switch is pressed while this switch is being pressed, a switch function can be added. Numeral 45 denotes a group of function switches which are used when selecting switches corresponding to switch displays which are displayed at predetermined positions in a lower portion of the screen of the display 30.

FIG. 3 is a block diagram for describing the control of the apparatus. A switch signal from the switch section 31 of the controller 5 is subjected to predetermined processing, and is then inputted to a microcomputer circuit 50. Connected to the microcomputer circuit 50 are a memory 51 for storing a control program such as an optometric program, as well as a memory 52 for storing measurement data and the like. The microcomputer circuit 50 converts the switch signal to various data on the basis of the control program stored in the memory 51, effects arithmetic processing, and controls the screen of the display 30 through a display circuit 53. In addition, the converted signal is inputted to a microcomputer circuit 55 of the relay unit 6. The microcomputer circuit 55 supplies data on refractive power to the subjective-type refractive-power measuring device 2 and supplies data on the target (chart) to the target (chart) presenting device 4.

A microcomputer circuit 60 of the subjective-type refractive-power measuring device 2 which has received the data on the refractive power drives motors 62 via drive circuits 61 to rotate a weak spherical lens disk 63, a strong spherical lens disk 64, an auxiliary lens disk 65, a cross-cylinder lens disk 66, and the like, thereby disposing predetermined optical systems in the test windows. In addition, the microcomputer circuit 60, upon receiving signals concerning the sliding and flapping of the lens units 10, drives drive motors 204 and 207.

A microcomputer circuit 70 of the target (chart) presenting device 4 which has received the data on the target (chart) lights up a lamp 72 for target (chart) projection, drives two motors 74 via two drive circuit 73, and drives a target (chart) disk 75 with a target (chart) depicted thereon and a mask disk 76, respectively, thereby projecting a predetermined test target (chart) onto an unillustrated screen placed in front of the eye being examined.

The objective-type refractive-power measuring device 3 and a lens meter 9 are connected to the microcomputer circuit 55, and measurement data sent to the microcomputer circuit 55 is stored in a memory 56. When a read command signal is inputted from the microcomputer circuit 50 on the controller 5 side to the microcomputer circuit 55, the microcomputer circuit 55 reads the designated measurement data from the memory 56 and transfers the same to the controller 5.

Numeral 57 denotes a printer for outputting the results of measurement, and 58 denotes a drive circuit thereof.

A description will be given of the operation of the apparatus having the above-described configuration. Here, a description will be given of the operation using an optometric program in which test items and a test procedure have been set in advance (see FIG. 4).

At the time of examination, when parameters are set and information on an inquiry after the subject is entered, a menu switch 32a of the group of setting changeover switches 32 is pressed. A set menu screen such as the one shown in FIG. 5 is displayed on the display 30. A reversely displayed portion can be moved by move switches 32b and 32c of the group of switches 32, and a reversely displayed item of display can be selected by an execute switch 32d.

Upon completion of the setting of necessary parameters and the entry of inquiry information, the start switch 35 is pressed to execute the optometric program. A message prompting the entry of measurement data by means of the objective-type refractive-power measuring device 3 is displayed on the display 30.

Input of Objective Value Data

Various objective value data such as an S value (spherical power), a C value (astigmatic power (cylindrical power)), an A value (angle of astigmatic axis (cylindrical axis)), and the like which are obtained from the objective-type refractive-power measuring device 3 are stored in the memory 56 via the microcomputer circuit 55 of the relay unit 6 by pressing the print switch of the objective-type refractive-power measuring device 3. Subsequently, if the data input switch 39 of the controller 5 is pressed, and the objective (AR) switch of the group of input-data designating switches 38 is then pressed, the objective value data stored in the memory 56 are transferred to and stored in an objective value memory area of the memory 52 on the controller 5 side. It should be noted that the input of the objective value data may be effected manually by the operation of the group of mode-change designating switches 37, the dial switch 42, or the like apart from the data transfer through communication.

Testing of Unaided Visual Acuity

Upon completion of the input of objective value data, the objective value data is automatically copied to a subjective value memory area, and the copied data (subjective value data=objective value data) is displayed in left and right display portions 81 in an example of the screen shown in FIG. 6. Subsequently, in terms of the test item, the operation proceeds to the testing of unaided visual acuity. The display screen of the display 30 is set to a mode in which the value of unaided visual acuity of the right eye can be automatically entered, and the subjective value data shifts to the left and right display portions 81. FIG. 6 is an example of display at this time. A present test item is displayed in a central display portion, and entry can be made for a measurement item which is reversely displayed.

This apparatus has the function of calculating a value of unaided visual acuity which is estimated on the basis of the objective value data, and when the testing of unaided visual acuity is started, an operation signal is issued to the target (chart) presenting device 4 to present a test target (chart) having a calculated value of estimated vision. An estimated value of unaided visual acuity is displayed in the VA column of the central display portion 80, and a target (chart) pattern 83 which is being presently presented is displayed in an operation explanation area 82 below the central display portion 80. The examiner applies a mask to the target (chart) by using switches 34a and 34b of the group of mask switches 34, obtains a value of unaided visual acuity of the eye being measured by changing the presented target (chart), and inputs the same. In this case, the test may be conducted by causing the subject to hold an eye cover without disposing the subjective-type refractive-power measuring device 2 in front of the eye being examined, or the test window of the measurement eye side may be opened with the other eye covered.

After the testing of the unaided visual acuity of the right eye is finished, the unaided visual acuity of the left eye and both eyes is tested in a similar manner. A highest value of visual acuity between the right and left eye is automatically displayed in the VA column of the central display portion 80, and the testing can be started from that value.

Input of Spectacle Data

After the unaided visual acuity values of both eyes have been inputted, the advance switch 36 is pressed to proceed to an ensuing test item. A message to the effect that the presence or absence of spectacles (including contact lenses) should be confirmed is displayed on the display 30, and the designation of switch operation based on the presence or absence of spectacles is displayed below the screen. If the function switch 45 for the presence of spectacles is pressed in compliance with the instruction, the mode is changed over to one in which the spectacle power data can be entered. In the same way as the objective value data, the entered spectacle power data is transferred from the lens meter 9 to the memory 56 and is stored therein, and if the input switch 39 and a spectacle (LM) switch of the group of switches 38 are pressed, the spectacle power data is stored in a former-spectacle memory area of the memory 52. It should be noted that in a case where the powers of spectacles have been entered in advance prior to the start of testing, this stage of input of spectacle power data is omitted.

Testing of Spectacled Visual Acuity

After the spectacle power data has been inputted, the screen of the display 30 is changed over to a mode of testing for confirmation of the spectacled visual acuity of the right eye. Since optical systems corresponding to the spectacle power data are disposed in the test windows of the subjective-type refractive-power measuring device 2, the test may be conducted by disposing the subjective-type refractive-power measuring device 2 in front of the subject's eyes. An estimated visual acuity value based on the residual power due to the difference between the objective value data and the spectacle power data is displayed in the VA column for the right eye in the central display portion 80, and a signal is issued to the target (chart) presenting device 4 to present a test target (chart) having that visual acuity value. A visual acuity value is obtained by changing over the presented target (chart) by means of the switches 34a and 34b on the basis of the response from the subject, and that value is inputted. If the test is conducted for the left eye and both eyes in a similar manner, visual acuity values are inputted in the same way as in the case of the testing of unaided visual acuity.

Subjective Value Test

After the above inputs have been made, the operation proceeds to the testing for determining perfect correction values (powers) for both eyes, respectively. In the optometric program of this embodiment, the following tests are conducted for each eye: an objective visual acuity confirmation test for confirming the appropriateness of objective value data, a first R/G (red/green) test which is carried out before the testing of astigmatism, an astigmatic-axis detection test, an astigmatic-power detection test, a second R/G test for obtaining maximum visual acuity while preventing over correction, and optometry. Subsequently, a binocular balance test is carried out to obtain values (powers) of monocular perfect correction (in this specification, respective monocular perfect correction values (powers) for left and right eyes which are obtained after conducting the binocular balance test are referred to as the values (powers) of binocular perfect correction). In these tests as well, the arrangement provided is such that, by pressing the advance switch 36, operation signals necessary for the tests are basically issued from the microcomputer circuit 50 to the subjective-type refractive-power measuring device 2 and the target (chart) presenting device 4, and the tests proceed consecutively (refer to German Patent Publication DE 197 28 186 A1). Values (powers) of binocular perfect correction and visual acuity values obtained in the tests are stored in the memory 52.

Adjustment of Correction Powers for Far Use

Subsequently, the operation proceeds to the adjustment of correction powers for far use. This apparatus has an automatic adjustment program whereby, if the values (powers) of binocular perfect correction and spectacle power data are available, powers which are estimated to be suitable for wearing by the subject by alleviating an uneasy sensation are automatically calculated on the basis of that data, as well as an automatic adjustment program whereby powers for securing visual acuity values desired by the subject are automatically calculated. This is because, when a pair of spectacles is prepared, prescription powers are usually determined which will alleviate an uneasy sensation so as to make the wearer be less fatigued (if the powers are made suddenly strong, the wearer is generally difficult to become accustomed to them and is liable to be fatigued, so that prescription powers are adjusted in spectacle shops by placing priority on the preparation of spectacles which will unlikely to result in complaints), but there are some wearers who desire to secure values of visual acuity to some extent (e.g., for securing visual acuity values for acquisition or renewal of a driver's license).

If the advance switch 36 is pressed, a screen for selecting either automatic adjustment program is displayed on the display 30, as shown in FIG. 7. The "POWER" program mode if powers for alleviating an uneasy sensation are to be obtained, and the "VISUAL ACUITY" program mode if powers for securing visual acuity are to be obtained, are selectively entered by the function switch 45 corresponding to that display.

(a) Adjustment of Correction Powers for Far Use with Priority On Powers

First, referring to flowcharts in FIGS. 8 to 13, a description will be given of the automatic adjustment program in which priority is placed on powers for alleviating an uneasy sensation. This program mode is executed by an input using the function switch 45 corresponding to the display of "POWER" in the example of the screen shown in FIG. 7. It should be noted that the term "a stronger eye" used in the description that follows refers to whichever has a greater absolute value in terms of the power of each of the S value and the C value between the perfect corrected both eyes. Meanwhile, the term "a weaker eye" refers to the opposite of the same. In addition, a minus reading is adopted for astigmatism (C value).

First, the apparatus determines the presence or absence of astigmatism on the basis of the values (powers) of binocular perfect correction (Step 1-1). If astigmatism is present, a determination is made as to whether or not astigmatism is oblique astigmatism (AXIS: 15° to 75° or 105° to 165°) (Step 1-2). Subsequently, on the basis of the S values of both eyes a determination is made as to hyperopia (both eyes are plus, or one eye is plus and the other eye is 0) or myopia (both eyes are minus, or one eye is minus and the other eye is 0) (Steps 1-3 to 1-5), so that adjusted powers can be calculated by effecting the processing of one of ensuing power adjustments A to F. When it is impossible to distinguish between hyperopia and myopia (then the S value of one eye is plus, and the S value of the other eye is minus), the power adjustment is not effected, and a message is displayed to the effect that the examiner is to make an adjustment.

Automatic Adjustment A: In the Case of Hyperopia Without Astigmatism

On the basis of the presence or absence of the input of spectacle power data (presence or absence of a history of spectacles), the apparatus determines whether or not the subject wears the spectacles for the first time (Step A-1). Thereafter, the same also applies to automatic adjustments B to F.

[A-1] If the subject wears the spectacles for the first time, the difference between the S values of the left and right eyes is then compared with a reference value (Step A-2). If the difference between the S values of the left and right eyes is within a predetermined power difference (hereafter, a description will be given under the assumption that the difference in the S value or the C value between the left and right eyes is to be adjusted to within 0.75 D), the values (powers) of binocular perfect correction are used as they are as adjusted powers. If the difference in the S value between the left and right eyes exceeds 0.75 D, the S value of the stronger eye is set to a value in which +0.75 D is added to the S value of the weaker eye (Step A-3).

[A-2] If the subject does not wear the spectacles for the first time, the difference in the S value between the left and right eyes is compared with the reference value (Step A-4). If the difference between the left and right eyes exceeds 0.75 D, the S value of the stronger eye is set to whichever value having a greater absolute value between a value in which +0.75 D is added to the S value of the weaker eye and a value in which a predetermined power (in the case of a hyperopia, +0.75 D hereafter) is added to the S value of the same side of the former spectacles, such that the value does not exceed the relevant one of the values (powers) of binocular perfect correction (Step A-5).

Automatic Adjustment B: In the Case of Myopia Without Astigmatism

[B-1] If the subject wears the spectacles for the first time, correction processing is first carried out in which a correction amount $\Delta S1$ is obtained by calculation in Table A in FIG. 14 by using as a reference the S value of the weaker eye obtained in binocular perfect correction, and the correction amount $\Delta S1$ is subtracted from each of the S values of binocular perfect correction for both eyes (hereafter, this processing will be referred to as correction processing A1) (Step B-2). Next, the difference between the left and right eyes after correction processing is compared with the reference value (Step B-3), and if the difference exceeds 0.75 D, the S value of the stronger eye is set to a value in which $-0.75$ D is added to the S value of the weaker eye (Step B-4).

[B-2] If the subject does not wear the spectacles for the first time, correction processing is carried out in which a correction amount $\Delta S2$ is obtained by calculation in Table B in FIG. 14 by using as a reference a smaller one of the differences between the former spectacle value (power) and the value (power) of binocular perfect correction in left and right S values, and the correction amount $\Delta S1$ is subtracted from each of the S values of binocular perfect correction for both eyes (hereafter, this processing will be referred to as correction processing B1) (Step B-5). Next, the difference in the S value between the left and right eyes after correction processing is compared with the reference value (Step B-6), and if the difference exceeds 0.75 D, the S value of the stronger eye is set to whichever value having a greater absolute value between a value in which $-0.75$ D is added to the S value of the weaker eye and a value in which a predetermined power (in the case of a myopia, $-0.75$ D hereafter) is added to the S value of the same side of the former spectacles, such that the value does not exceed the relevant one of the values (powers) of binocular perfect correction (Step B-7).

Automatic Adjustment C: In the Case of Hyperopia Having Astigmatism Which Is Not Oblique Astigmatism

[C-1] If the subject wears the spectacles for the first time, correction processing is first carried out in which a correction amount $\Delta C1$ is obtained by calculation in Table C in FIG. 14 by using as a reference the C value of the weaker eye, and the correction amount $\Delta C1$ is subtracted from each of the C values of binocular perfect correction for both eyes (hereafter, this processing will be referred to as correction processing C1) (Step C-2). Then, the S values of both eyes are each set to a value in which half of the correction amount $\Delta C1$ is added to the value (power) of binocular perfect correction to obtain a spherical equivalent value (Step C-3). Subsequently, the difference between the obtained S values of the left and right eyes is compared with the reference value (Step C-4), and if the difference exceeds 0.75 D, the S value of the stronger eye is set to a value in which +0.75 D is added to the S value of the weaker eye (Step C-5). Next, the difference in the C value between the left and right eyes after the correction processing C1 is compared with the reference value (Step C-6), and if the difference exceeds 0.75 D, the C value of the stronger eye is set to a value in which $-0.75$ D is added to the C value of the weaker eye (Step C-7).

[C-2] In a case where the subject does not wear the spectacles for the first time, first, if astigmatism is not present on the basis of the determination of the presence or absence of stigmatism in the former spectacle values (powers) (Step C-8), the same power adjustment as in the case of the initial wearing is performed (Steps C-2 to C-7). If astigmatism is present, correction processing is carried out in which a correction amount $\Delta C2$ is obtained by calculation in Table D in FIG. 14 by using as a reference a smaller one of the differences between the former spectacle value (power) and the value (power) of binocular perfect correction in left and right C values, and the correction amount $\Delta C2$ is subtracted from each of the C values of binocular perfect correction for both eyes (hereafter, this processing will be referred to as correction processing D1) (Step C-9). Then, the S values of both eyes are each set to a value in which half of the correction amount $\Delta C2$ is added to the value (power) of binocular perfect correction to obtain a spherical equivalent value (Step C-10). Subsequently, the difference between the obtained S values of the left and right eyes is compared with the reference value (Step C-11), and if the difference exceeds 0.75 D, the S value of the stronger eye is set to whichever value having a greater absolute value between a value in which +0.75 D is added to the S value of the weaker eye made spherically equivalent and a value in which +0.75 D is added to the S value of the same side of the former spectacles, such that the value does not exceed the relevant one of the values (powers) of binocular perfect correction (Step C-12). Next, if the difference in the C value between the left and right eyes after the correction processing D1 exceeds 0.75 D (Step C-13), the C value of the stronger eye is set to whichever value having a greater absolute value between a value in which $-0.75$ D is added to the C value of the weaker eye and a value in which $-0.75$ D is added to the C value of the same side of the former spectacles, such that the value does not exceed the relevant one of the values (powers) of binocular perfect correction (Step C-14).

Automatic Adjustment D: In the Case of Myopia Having Astigmatism Which Is Not Oblique Astigmatism

[D-1] If the subject wears the spectacles for the first time, the correction processing C1 is carried out (Step D-2), and the correction processing A1 is carried out (Step D-3). Subsequently, the difference between the obtained S values of the left and right eyes is compared with the reference value (Step D-4), and if the difference exceeds 0.75 D, the S value of the stronger eye is set to a value in which $-0.75$ D is added to the S value of the weaker eye (Step D-5) Next, the difference in the C value between the left and right eyes after the correction processing C1 is compared with the reference value (Step D-6), and if the difference exceeds 0.75 D, the C value of the stronger eye is set to a value in which $-0.75$ D is added to the C value of the weaker eye (Step D-7).

[D-2] In a case where the subject does not wear the spectacles for the first time, first, a determination is made as to the presence or absence of stigmatism in the former spectacle values (powers) (Step D-8). If astigmatism is present, the correction processing D1 is effected (Step D-9). Then, the correction processing B1 is carried out (Step D-10). Subsequently, the difference between the obtained S values of the left and right eyes is compared with the reference value (Step D-11), and if the difference exceeds 0.75 D, the S value of the stronger eye is set to whichever value having a greater absolute value between a value in which −0.75 D is added to the S value of the weaker eye and a value in which −0.75 D is added to the S value of the same side of the former spectacles, such that the value does not exceed the relevant one of the values (powers) of binocular perfect correction (Step D-12). Next, the difference in the C value between the left and right eyes after the correction processing D1 is compared with the reference value (Step D-13), and if the difference exceeds 0.75 D (Step D-13), the C value of the stronger eye is set to whichever value having a greater absolute value between a value in which −0.75 D is added to the C value of the weaker eye and a value in which −0.75 D is added to the C value of the same side of the former spectacles, such that the value does not exceed the relevant one of the values (powers) of binocular perfect correction (Step D-14).

If astigmatism is not present in the determination on the presence or absence of astigmatism of the former spectacle values (powers), the correction processing C1 and the correction processing B1 are carried out (Steps D-15 and D-16). Subsequently, the difference between the obtained S values of the left and right eyes is compared with the reference value (Step D-17), and if the difference exceeds 0.75 D, the S value of the stronger eye is set to whichever value having a greater absolute value between a value in which −0.75 D is added to the S value of the weaker eye and a value in which −0.75 D is added to the S value of the same side of the former spectacles, such that the value does not exceed the relevant one of the values (powers) of binocular perfect correction (Step D-18). Next, if the difference in the C value between the left and right eyes after the correction processing C1 exceeds 0.75 D, the C value of the stronger eye is set to a value in which −0.75 D is added to the C value of the weaker eye (Steps D-19 and D-20).

Automatic Adjustment E: In the Case of Hyperopia Having Oblique Astigmatism

[E-1] If the subject wears the spectacles for the first time, a determination is made as to whether or not both C values of the left and right eyes are less than or equal to −0.50 D (hereafter, the C value being less than or equal to −0.50 D refers to a smaller power, i.e., −0.25 D or −0.50 D) (Step E-2). In the case of oblique astigmatism, if the C value is small, it is in many cases more desirable not to effect the correction of astigmatism for the subject. Therefore, if both C values of the left and right eyes are less than or equal to −0.50 D, it is assumed that astigmatism is negligible, so that the C values=0, and the S values for left and right are each set to a value in which half of the C value is added to the S value to obtain a spherical equivalent value (Step E-3). Subsequently, the difference between the obtained S values of the left and right eyes is compared with the reference value (Step E-4), and if the difference exceeds 0.75 D, the S value of the stronger eye is set to a value in which +0.75 D is added to the S value of the weaker eye (Step E-5).

In the determination (Step E-2) as to whether or not the C values are less than or equal to −0.50 D, if at least one of the left and right C values exceeds −0.50 D, the correction processing C1 is carried out (Step E-6), and the S values for left and right are each set to a value in which half of the correction amount ΔC1 is added to the value (power) of binocular perfect correction to obtain a spherical equivalent value (Step E-7). Subsequently, if the difference between the obtained S values of the left and right eyes exceeds 0.75 D, the S value of the stronger eye is set to a value in which +0.75 D is added to the S value of the weaker eye (Steps E-8 and E-9). Next, if the difference in the C value between the left and right eyes after the correction processing C1 exceeds 0.75 D, the C value of the stronger eye is set to a value in which −0.75 D is added to the C value of the weaker eye (Steps E-10 and E-11).

[E-2] If the subject does not wear the spectacles for the first time, a determination is made as to whether or not both C values of the left and right eyes are less than or equal to −0.50 D (Step E-12). Then, a determination is made as to whether or not the respective former spectacle values (powers) have astigmatism, respectively (Steps E-13 and E-14).

If both C values of binocular perfect correction are within −0.50 D, and the former spectacle values (powers) do not have astigmatism, a setting is provided such that the C values=0, and the S values for left and right are each set to a value in which half of the C value is added to the S value to obtain a spherical equivalent value (Step E-15). Subsequently, the difference between the obtained S values of the left and right eyes is compared with the reference value (Step E-16), and if the difference exceeds 0.75 D, the S value of the stronger eye is set to whichever value having a greater absolute value between a value in which +0.75 D is added to the S value of the weaker eye made spherically equivalent and a value in which +0.75 D is added to the S value of the same side of the former spectacles, such that the value does not exceed the relevant one of the values (powers) of binocular perfect correction (Step E-17).

If the former spectacle values (powers) have astigmatism in spite of the C values of binocular perfect correction, processing similar to that in Steps C-9 to C-14 is carried out (Step E-18 to E-23).

If at least one of the left and right C values exceeds −0.50 D, and the former spectacle values (powers) do not have astigmatism, the correction processing C1 is carried out (Step E-24), and the S values of both eyes are each set to a value in which half of the correction amount ΔC1 is added to the value (power) of binocular perfect correction to obtain a spherical equivalent value (Step E-25). Subsequently, the difference between the obtained S values of the left and right eyes is compared with the reference value (Step E-26), and if the difference exceeds 0.75 D, processing similar to that in Step C-12 is carried out (Step E-27). Next, the difference in the C value between the left and right eyes after the correction processing C1 is compared with the reference value (Step E-28), and if the difference exceeds 0.75 D, the C value of the stronger eye is set to a value in which −0.75 D is added to the C value of the weaker eye (Step E-29).

Automatic Adjustment F: In the Case of Myopia Having Oblique Astigmatism

[F-1] If the subject wears the spectacles for the first time, a determination is made as to whether or not both C values of the left and right eyes are less than or equal to −0.50 D (Step F-2). If both C values are within −0.50 D, both C values are set such that C values=0 (Step F-3). Then, the correction processing A1 is carried out for the S values (Step F-4). Subsequently, the difference between the obtained S values of the left and right eyes is compared with the reference value (Step F-5), and if the difference between the left and right eyes exceeds 0.75 D, the S value of the stronger eye is set to a value in which −0.75 D is added to the S value of the weaker eye (Step F-6).

In the determination (Step F-2) as to whether or not the C values are less than or equal to −0.50 D, if at least one of the left and right C values exceeds −0.50 D, the correction processing C1 is carried out (Step F-7). Then, the correction processing A1 is carried out for the S values (Step F-8).

Subsequently, the difference between the obtained S values of the left and right eyes is compared with the reference value (Step F-9), and if the difference between the left and right eyes exceeds 0.75 D, the S value of the stronger eye is set to a value in which −0.75 D is added to the S value of the weaker eye (Step F-10). Next, the difference in the C value between the left and right eyes after the correction processing C1 is compared with the reference value (Step F-11), and if the difference exceeds 0.75 D, the C value of the stronger eye is set to a value in which −0.75 D is added to the C value of the weaker eye (Steps F-12).

[F-2] If the subject does not wear the spectacles for the first time, a determination is made as to whether or not both C values of the left and right eyes are less than or equal to −0.50 D (Step F-13). Then, a determination is made as to whether or not the respective former spectacle values (powers) have astigmatism (C value), respectively (Steps F-14 and F-15).

If both C values of binocular perfect correction are within −0.50 D, and the former spectacle values (powers) do not have astigmatism, a setting is provided such that the C values=0 (F-16).

Subsequently, the correction processing B1 is carried out (Step F-17). Then, the difference between the obtained S values of the left and right eyes is compared with the reference value (Step F-18), and if the difference between the left and right eyes exceeds 0.75 D, processing similar to that in Step B-7 is carried out for the S value of the stronger eye (Step F-19).

If the former spectacle values (powers) have astigmatism in spite of the C values of binocular perfect correction, processing similar to that in Steps D-9 to D-14 is carried out (Step F-20 to F-25).

If at least one of the left and right C values exceeds −0.50 D, and the former spectacles values (powers) do not have astigmatism, the correction processing C1 is carried out for the C values (Step F-26), and the correction processing B1 is carried out for the S values (Step F-27). Subsequently, the difference between the obtained S values of the left and right eyes is compared with the reference value (Step F-28), and if the difference between the left and right eyes exceeds 0.75 D, processing similar to that in Step B-7 is carried out for the S value of the stronger eye (Step F-29). Next, the difference in the C value between the left and right eyes after the correction processing C1 is compared with the reference value (Step F-30), and if the difference between the left and right eyes exceeds 0.75 D, the C value of the stronger eye is set to a value in which −0.75 D is added to the C value of the weaker eye (Step F-31).

In the above-described manner, when it is possible to distinguish between hyperopia and myopia, the apparatus effects the processing of one of automatic adjustment A to F, and automatically calculates powers which are estimated to be optimally suited.

It should be noted that although, in the above-described automatic adjustment program, as for the adjustment amount for adjusting the S value or the C value of the stronger eye, in a case where a change from the former spectacle of the same side is adopted, adjustment of ±0.75 D (three steps) is made with respect to the S value or the C value (Steps A-5, B-7, C-14, etc.), an arrangement may be provided such that an adjustment amount of ±0.50 D (two steps) is varied depending on the age of the subject. The reason for this is that there are differences in the adaptive capability with respect to the change in the powers of the former spectacles depending on the age. A young person is capable of adapting himself or herself even if there is a change of three steps (0.75 D) with respect to the powers of former spectacles, but as the age becomes higher, a change of two steps (0.50 D) generally becomes a limit in adaptation. Accordingly, if an attempt is made to change the adjustment amount of the prescription powers depending on the adaptive capability of the eye being examined, it is possible to provide a prescription which is more suitable for the wearer. An arrangement is provided such that changes in the amount of the power can be inputted prior to the execution of the automatic adjustment program.

Furthermore, although, in the above-described embodiment, the correction amounts $\Delta S1$, $\Delta S2$, $\Delta C1$, and $\Delta C2$ in the correction processing A1 to D1 are obtained by calculation, tables may be prepared in advance respectively, and the correction amounts $\Delta S1$, $\Delta S2$, $\Delta C1$, and $\Delta C2$ in the correction processing A1 to D1 may be obtained on the basis of the tables.

In the above-described automatic adjustment program, the power of astigmatism is calculated by dividing astigmatism into two types, i.e., whether or not astigmatism is oblique astigmatism (AXIS: 15° to 75° or 105° to 165°). However, in a case where the case is not oblique astigmatism, if the method of calculation of the adjusted power is changed depending on either astigmatism with the rule(AXIS: 0° to 14° or 166° to 180°) or astigmatism against the rule(AXIS: 74° to 104°), more accurate adjustment is made possible, and an attempt can be made to reduce the pain of the subject and complaints. This is ascribable to the following reason.

Optometry is generally conducted by means of a test for far use at 5 m or the like, and the astigmatic power obtained therefrom is used for a spectacle not only for far use but also for near use. When a near object is viewed, the accommodative power functions, and the crystalline lens in the eye swells, resulting in a change in the astigmatic power. Physiologically, the crystalline lens of a human is astigmatic against the rule (i.e., the state in which light is more strongly bent in the horizontal direction than in the vertical direction), and if the accommodative power functions, the rate of astigmatism against the rule often increases. For this reason, as for the astigmatic power in the far distance, in the case of astigmatism with the rule the astigmatism becomes weaker when a near object is viewed, whereas in the case of astigmatism against the rule the astigmatism becomes stronger. Spectacles or the like are used for viewing not only objects in the far distance but those located at distances ranging from the far distance to the near distance (rather, they are more frequently used to view objects in the near distance). If the effect of correction of astigmatism at the time of viewing objects in the near distance is considered, it is advisable to prescribe a slightly weaker power in the case of astigmatism with the rule and a slightly stronger power (close to a value (power) of perfect correction) in the case of astigmatism against the rule. In addition, as another reason, it is possible to cite the fact that a greater burden is said to be liable to be imposed on accommodation in the case of astigmatism against the rule than in the case of astigmatism with the rule, and since it can cause eyestrain, it is generally said that the power should be set close to a value (power) of perfect correction.

Accordingly, a description will be given of a power adjustment program which takes into consideration the cases of astigmatism with the rule and astigmatism against the rule by making use of the above-described characteristic (see FIGS. 15 to 17). As a result of determination as to whether or not the case is oblique astigmatism (Step 1-2), if it is determined that the case is not oblique astigmatism, a determination is made as to whether or not the case is astigmatism with the rule (Step 2-1). In the case of astigmatism with the rule, the adjusted powers are calculated in accordance with the procedure in and after Step 1-4 in the same way as described above. If the case is not astigmatism with the rule (in the case of astigmatism against the rule), on the basis of the S values of both eyes a determination is first made as to hyperopia (both eyes are plus, or one eye is plus and the other eye is 0) or myopia (both eyes are minus, or one eye is minus and the other eye is 0) (Step 2-2), and an automatic adjustment 2C shown in FIG. 16 or an automatic adjustment 2D shown in FIG. 17 is performed. The C value in the automatic adjustment in this case remains as the value (power) of binocular perfect correction, and only the S value is adjusted in the same way as in the above-described automatic adjustments C and D.

This method can be changed as described below. For example, when the difference in the C value between the left and the right is taken into consideration, the stronger eye side maybe adjusted so as to fall into the ranges of three steps by using the weaker eye as a reference.

Alternatively, in Tables C and D shown in FIG. 14 which are used in the automatic adjustment programs in the case of astigmatism with the rule(the automatic adjustment C in FIG. 10 and the automatic adjustment D in FIG. 11), an arrangement may be provided such that the respective correction amounts $\Delta C1$ and $\Delta C2$ are made smaller so as to cause the adjusted power of the C value to become closer to the value (power) of perfect correction. That is, arithmetic expressions for determining the correction amounts $\Delta C1$ and $\Delta C2$ in Tables C and D are changed as follows.

$$C1/2 \rightarrow C1/3, C1/4, \text{etc.}$$

$$C2/2 \rightarrow C2/3, C2/4, \text{etc.}$$

In addition, if an arrangement is provided such that a change in the amount of adjustment of the C value in the case of such astigmatism with the rule can be set freely by the examiner in the menu for setting parameters, adjusted powers which better conform to the examiner's policy of examination can be favorably calculated.

(b) Adjustment of Correction Powers for Far Use with Priority On Visual Acuity

Next, a description will be given of the automatic adjustment program in the case where priority is placed on visual acuity desired by the wearer. If the function switch 45 corresponding to the display of "VISUAL ACUITY" in the example of the screen shown in FIG. 7, a screen is newly displayed for allowing a desired visual acuity value to be inputted, as shown in FIG. 18. The input of the visual acuity value is effected by operating the dial switch 42. It should be noted that, in this case, an arrangement is provided such that a visual acuity value higher than the visual acuity value obtained at the time of determination of the perfect correction value (power) cannot be inputted.

When the desired visual acuity value has been inputted, if the function switch 45 corresponding to the display of "EXECUTE" in the lower portion of the screen is pressed, the automatic adjustment program is executed. The calculation of the power for the desired visual acuity value is effected in accordance with the table shown in FIG. 19. In the table for calculation of the power, the power D0 which is subtracted from the perfect correction value (power) is made to correspond to the desired visual acuity value VA2 for each visual acuity value VA1 at the time of determination of the perfect correction value (power). For example, when the visual acuity value VA1 at the time of determination of the perfect correction value (power) was 1.0, and the S value of perfect correction was −3.75 (D), if the desired visual acuity value VA2 was 0.8, then the power D0 which is obtained in the table is −0.25 (D), so that −0.25 (D) is subtracted from −3.75 (D), thereby setting the adjusted power as −3.50 (D). Although this table is common to both the S value and the C value, an exclusively used table may be provided separately for the C value. Instead of using the table, mathematical expressions may be formed for powers with respect to desired visual acuity values.

Further, an arrangement may be provided such that the power with respect to the desired visual acuity value is calculated by making the desired visual acuity value correspond to a visual acuity value based on the former spectacle value (power) (unaided visual acuity value in the case of the initial wearer) and the visual acuity value obtained at the time of determination of the perfect correction value (power). If such an arrangement is adopted, it is possible to calculate more appropriate powers in correspondence with the individual refractive powers of the subjects.

In addition, the power with respect to the desired visual acuity value may be calculated as follows. After execution of the above-described automatic adjustment program in the adjustment of correction powers for far use with priority on powers, a determination is made as to whether or not the visual acuity value desired by the subject can be secured by the power thus calculated, and if the visual acuity value can be secured, it suffices if that adjusted power is used. Alternatively, if the power based on the desired visual acuity value is weaker (closer to the power of the former spectacle) than the power obtained in the above-described adjustment with priority on powers, there are cases where the subject becomes accustomed to the spectacle more easily, which is favorable, so that the value may be kept intact. Meanwhile, if it is impossible to secure the visual acuity value desired by the subject, the power of such a portion that makes it possible to secure the desired visual acuity value is incorporated on the basis of the calculated power. The power which is incorporated can be determined by a table prepared in advance or a calculation.

Adjustment of Powers by the Examiner

As a result of execution of the automatic adjustment program, its results are displayed on the display 30. FIG. 20 is a diagram illustrating an example of the screen of the display 30 after the automatic adjustment. The central display portion 80 is changed to the prescription mode, automatically adjusted powers are displayed as the S values and the C values on the display by the apparatus, and a message to the effect that powers for far use have been adjusted is displayed in the lower portion of the central display portion 80. Optical systems corresponding to the automatically adjusted powers are set in the test windows of the subjective-type refractive-power measuring device 2, and visual acuity value targets (charts) having a set of targets (charts) with visual acuity values ranging from 0.9 to 1.2 are presented from the target (chart) presenting device (when desired visual acuity values have been inputted, targets (charts) having the visual acuity values are automatically presented). While confirming the appearance of the adjusted powers, the examiner makes fine adjustment of the correction powers for far use by means of the switch operation.

The apparatus has a control program for manual adjustment whereby the power of the item to be adjusted is changed if a switch input is made on the basis of the hyperopia or myopia, the presence or absence of astigmatism, and the presence or absence of oblique astigmatism which are provided by the powers calculated by the automatic adjustment program (see FIGS. 21 and 22). When the automatic adjustment program has been executed, if the changeover switch 43a or 43b is operated after obtaining a response from the subject on the appearance, the power of the item to be adjusted is automatically adjusted. As for the details of this control program, reference should be made to German Patent Publication DE 197 28 186 A1. The results of fine adjustment by the examiner are stored in the memory 52.

After adjustment of the correction values for far use have been made, a test for near use is conducted as necessary, prescription powers are determined, and the results of the examination are printed out, thereby completing the subjective examination.

The results of each subject thus obtained are stored in the memory 52 (or the memory 56 on the relay unit 6 side when there is a limit to the storage capacity). The results of such examinations are stored with respect to a multiplicity of subjects, and if the results of the multiplicity of examinations are statistically processed and are fed back to the method of calculating the power through the automatic adjustment program, it becomes possible to allow the apparatus to calculate values which are closer to the values which are finely adjusted by the examiner. A description will be given of this method.

In the above-described automatic adjustment programs (those shown in the flowcharts in FIGS. 8 to 13), adjustment of the S value and the C value is made on the basis of correction processing A1 to D1. Calculating expressions used in these items of correction processing can be rephrased as follows:

S value after correction=S value of binocular perfect correction−(S value of binocular perfect correction−S value of the former spectacle)/2     (Mathematical Formula 1)

C value after correction=C value of binocular perfect correction−(C value of binocular perfect correction−C value of the former spectacle)/2     (Mathematical Formula 2)

In the case of the initial wearer, it suffices if a setting is provided such that the S value of the former spectacle and the C value of the former spectacle=0.

Here, the terms for calculating the correction amount in Mathematical Formulae 1 and 2 are respectively multiplied by correction coefficients $\alpha$ and $\beta$ serving as variables, and we have S value after correction=S value of binocular perfect correction−{(S value of binocular perfect correction−S value of the former spectacle)/2}$\alpha$     (Mathematical Formula 3)

C value after correction=C value of binocular perfect correction−{(C value of binocular perfect correction−C value of the former spectacle)/2}$\beta$     (Mathematical Formula 4)

These correction coefficients $\alpha$ and $\beta$ are correction coefficients for filling the gap between the adjusted power calculated by the automatic adjustment program and the prescription power obtained by the fine adjustment made by the examiner (initial values of the correction coefficients $\alpha$ and $\beta$ being set to 1).

The prescription powers after the fine adjustment by the examiner and the binocular perfect correction values (powers), the components of the respective S value and the C value thereof, together with those of the former spectacle values (powers), if available, are applied to the above-described Mathematical Formulae 3 and 4, and the respective correction coefficients $\alpha$ and $\beta$ are determined. When data of a multiplicity of subjects (the greater the number of samples, such as 100 to 1000 subjects, the more advantageous) has been gathered, average values of the respective correction coefficients $\alpha$ and $\beta$ are calculated, and are fed back to Mathematical Formulae 3 and 4, which are used in the correction processing A1 to D1 in the automatic adjustment program. As a result, the adjusted powers calculated in the automatic adjustment program are made to approach to the powers obtained by the fine adjustment by the examiner, allowing powers preferred by the examiner to be calculated by each apparatus. Accordingly, the fine adjustment after the automatic adjustment progresses smoothly, thereby making it possible to improve the examination efficiency.

It should be noted that the feedback of the correction coefficients $\alpha$ and $\beta$ determined by for each subject may be effected after a certain volume of a multiplicity of pieces of data has been gathered (this is effective such as when the examiner in charge of the apparatus has been changed), and the feedback may also be effected from the outset each time data is obtained.

What is claimed is:

1. An optometric apparatus for obtaining a correction power correcting ametropia based on a refractive power of a subject eye, said apparatus comprising:

data input means for inputting a perfect correction power of a subject eye and adjustment factor data for adjusting the correction power;

program storing means for storing a program used for estimating a prescription power by making adjustments to the correction power in relation to the perfect correction power on the basis of the adjustment factor data inputted by said data input means, said program including a step of obtaining a correction amount used in making adjustments to the correction power;

data storing means for storing a multiplicity of actual prescription powers, and perfect correction powers and adjustment factor data on the basis of which an examiner determined the actual prescription power in the past, respectively;

first calculating means for obtaining a variable coefficient for making variable the correction amount in said program by statistically processing a multiplicity of data stored in said data storing means;

program advancing means for advancing said program;

second calculating means for determining an estimated prescription power in accordance with said program and on the basis of the variable correction amount obtained by said first calculating means; and display means for displaying the estimated prescription power determined by said second calculating means.

2. An optometric apparatus according to claim 1, wherein said data input means inputs the perfect correction power of the subject eye, a visual acuity value of the subject eye when its power is corrected to the perfect correction power, and a desired visual acuity value desired by a subject for the subject eye, wherein said program further includes a step of estimating a prescription power by making adjustments to the correction power to secure said desired visual acuity value on the basis of the perfect correction power, the visual acuity value and the desired visual acuity value inputted by said data input means, and wherein said program advancing means includes selecting means for selecting whether or not said step of estimating a prescription power by making adjustments to the correction power to secure said desired visual acuity value is executed.

3. An optometric apparatus according to claim 2,
wherein said data input means further inputs a power of a former spectacle and a visual acuity value obtained when the subject wears the former spectacle, and
wherein said step of estimating a prescription power by making adjustments to the correction power to secure said desired visual acuity value estimates the prescription power by making adjustments to the correction power to secure said desired visual acuity value on the basis of the perfect correction power of the subject eye, the visual acuity value of the subject eye when its power is corrected to the perfect correction power, the desired visual acuity value desired by a subject for the subject eye, the power of the former spectacle and the visual acuity value obtained when the subject wears the former spectacle.

4. An optometric apparatus according to claim 1, further comprising:
correction-amount storing means for storing as a correction table the correction amount used in making adjustments to the correction power, and
wherein said program estimates the prescription power by making adjustments to the correction power with the correction amount obtained from said correction table.

5. An optometric apparatus according to claim 1, wherein said program further includes a step of obtaining one of different adjustment powers depending on whether a kind of astigmatism of the perfect correction power is oblique astigmatism, astigmatism with the rule, or astigmatism against the rule.

6. An optometric apparatus according to claim 5, wherein said program further includes a step of setting the adjustment power as the perfect correction power of astigmatism if the kind of astigmatism is astigmatism against the rule.

7. An optometric apparatus according to claim 5, wherein said program further includes a step of setting the adjustment power to a power which is closer to the perfect correction power than the adjustment power for the astigmatism with the rule is if the kind of astigmatism is astigmatism against the rule.

8. An optometric apparatus for obtaining a correction power correcting ametropia based on a refractive power of a subject eye, said apparatus comprising:
data input means for inputting a perfect correction power of a subject eye and adjustment factor data for adjusting the correction power;
program storing means for storing a program used for estimating a prescription power by making adjustments to the correction power in relation to the perfect correction power on the basis of the adjustment factor data inputted by said data input means, said program including a step of obtaining one of different adjustment powers depending on whether a kind of astigmatism of the perfect correction power is oblique astigmatism, astigmatism with the rule, or astigmatism against the rule;
program advancing means for advancing said program;
prescription-power calculating means for determining an estimated prescription power in accordance with said program; and
display means for displaying the estimated prescription power determined by said prescription-power calculating means.

9. An optometric apparatus according to claim 8, wherein said program further includes a step of setting the adjustment power as the perfect correction power of astigmatism if the kind of astigmatism is astigmatism against the rule.

10. An optometric apparatus according to claim 8, wherein said program further includes a step of setting the adjustment power to a power which is closer to the perfect correction power than the adjustment power for the astigmatism with the rule if the kind of astigmatism is astigmatism against the rule.

11. An optometric apparatus for obtaining a correction power correcting ametropia based on a refractive power of a subject eye, said apparatus comprising:
perfect-correction-value input means for inputting a perfect correction power of a subject eye and a visual acuity value of the subject eye when its power is corrected to the perfect correction power;
desired-visual-acuity-value input means for inputting a desired visual acuity value desired by a subject for the subject eye;
program storing means for storing a program used for estimating a prescription power, said program including a first step of estimating the prescription power by making adjustments to the correction power to secure said desired visual acuity value on the basis of the perfect correction power, the visual acuity value and the desired visual acuity value inputted by both said input means;
program advancing means for advancing said program;
prescription-power calculating means for determining an estimated prescription power in accordance with said program; and
display means for displaying the estimated prescription power determined by said prescription-power calculating means.

12. An optometric apparatus according to claim 11, further comprising:
former-spectacle-value input means for inputting a power of a former spectacle and a visual acuity value obtained when the subject wears the former spectacle,
wherein said first step estimates the prescription power by making adjustments to the correction power to secure said desired visual acuity value on the basis of the perfect correction power of the subject eye, the visual acuity value of the subject eye when its power is corrected to the perfect correction power, the desired visual acuity value desired by a subject for the subject eye, the power of the former spectacle and the visual acuity value obtained when the subject wears the former spectacle.

13. An optometric apparatus according to claim 11, further comprising:
correction-amount storing means for storing as a correction table an correction amount used in making adjustments to the correction power, and
wherein said first step estimates the prescription power by making adjustments to the correction power with the correction amount obtained from said correction table.

14. An optometric apparatus according to claim 11, further comprising:
data input means for inputting adjustment factor data for adjusting the correction power,
wherein said program includes a second step of estimating a prescription power by making adjustments to the correction power in relation to the perfect correction power on the basis of the adjustment factor data inputted by said data input means, and
wherein said program advancing means includes selecting means for selectively executing either one of said first and second steps.

* * * * *